(12) United States Patent
Watson et al.

(10) Patent No.: US 11,288,847 B2
(45) Date of Patent: Mar. 29, 2022

(54) DOUBLE SCATTER SIMULATION FOR IMPROVED RECONSTRUCTION OF POSITRON EMISSION TOMOGRAPHY DATA

(71) Applicant: Siemens Medical Solutions USA, Inc., Malvern, PA (US)

(72) Inventors: Charles C. Watson, Knoxville, TN (US); Jicun Hu, Knoxville, TN (US); Chuanyu Zhou, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 432 days.

(21) Appl. No.: 16/598,277

(22) Filed: Oct. 10, 2019

(65) Prior Publication Data

US 2020/0151918 A1 May 14, 2020

Related U.S. Application Data

(60) Provisional application No. 62/757,893, filed on Nov. 9, 2018.

(51) Int. Cl.
| | |
|---|---|
| *G06T 11/00* | (2006.01) |
| *G01T 1/29* | (2006.01) |
| *A61B 6/00* | (2006.01) |
| *A61B 6/03* | (2006.01) |

(52) U.S. Cl.
CPC ............ *G06T 11/005* (2013.01); *A61B 6/037* (2013.01); *A61B 6/4291* (2013.01); *A61B 6/5282* (2013.01); *G01T 1/2985* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 7,312,455 B2 | 12/2007 | Manjeshwar et al. | |
| 7,397,035 B2 | 7/2008 | Watson | |
| 7,714,291 B2* | 5/2010 | Thielemans | G01T 1/2985 250/363.03 |
| 11,069,097 B1* | 7/2021 | Elran | G06T 7/0016 |
| 2005/0072929 A1 | 4/2005 | Chuang et al. | |
| 2006/0163485 A1* | 7/2006 | Stearns | G01T 1/2985 250/363.03 |
| 2010/0219346 A1 | 9/2010 | Daghighian | |
| 2011/0210255 A1* | 9/2011 | Kim | G01T 1/2985 250/362 |
| 2017/0016999 A9 | 1/2017 | Nelson et al. | |
| 2018/0136340 A1 | 5/2018 | Nelson et al. | |
| 2021/0199823 A1* | 7/2021 | Li | G01T 7/005 |

OTHER PUBLICATIONS

M Conti, B Bendriem, M Casey, M Chen, F Kehren, C Michel and V Panin, "Implementation of Time-Of-Flight on CPS HiRez PET scanner." In: 2004 IEEE Nuclear Science Symposium Conference Record [book on CD-ROM]. Piscataway, N.J.: IEEE; 2004:M3-1.

* cited by examiner

*Primary Examiner* — Hoon K Song

(57) ABSTRACT

Methods for simulating, and correcting for, doubly scattered annihilation gamma-ray photons in both time-of-flight (TOF) and non-TOF positron emission tomography scan data are disclosed.

18 Claims, 16 Drawing Sheets

DOUBLE SCATTER SIMULATION FOR IMPROVED RECONSTRUCTION OF POSITRON EMISSION TOMOGRAPHY DATA

CROSS-REFERENCE TO RELATED APPLICATIONS

This application claims priority under 35 U.S.C. § 119(e) to U.S. Provisional Application No. 62/757,893, filed Nov. 9, 2018, the entire contents of which are incorporated herein by reference.

FIELD

The present disclosure generally relates to nuclear medicine, and systems for obtaining nuclear medicine images. In particular, the present disclosure relates to systems and methods for reconstructing nuclear medicine images from time-of-flight (TOF) positron emission tomography (PET) data.

BACKGROUND

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred. An example of a PET method and apparatus is described in U.S. Pat. No. 6,858,847, which patent is incorporated herein by reference in its entirety.

After being integrated and sorted into LORs defined by the positions of the detectors in the PET camera, the coincidence event data are used to reconstruct a three-dimensional distribution of the positron-emitting radionuclide within the patient. In two-dimensional PET, each 2D transverse (perpendicular to the axis of the PET scanner) section or "slice" of the radionuclide distribution is reconstructed independently of adjacent sections, using only LORs that are (approximately) perpendicular to the axis of the scanner (referred to as the z axis). In fully three-dimensional PET, nearly all the LOR data are used for the reconstruction. The positions of these LORs in space are characterized by their radial distance, s, from the z axis, their azimuthal angle, $\Phi$, around the z axis, their polar angle, $\Theta$, with respect to the z axis, and the z position of their closest approach to the z axis. These LOR data are typically arranged into a set of "sinograms", $p(s, \Phi; \Theta, z)$, which, for fixed values of $\Theta$ and z, represents a two dimensional parallel projection of the three dimensional radionuclide distribution within the patient. All of the LORs in the sinogram $p(s, \Phi)$ having fixed values of $\Theta$ and z are essentially co-planar. In this format, a single fixed point in the emitter distribution $f(x,y,z)$ that falls within this $(\Theta, z)$ plane traces a sinusoid in the sinogram. In each sinogram, there is one row containing the LORs for a particular azimuthal angle $\Phi$; each such row corresponds to a one-dimensional parallel projection of the tracer distribution at a different projection angle. This is shown conceptually in FIG. 1 for case in which the plane of the sinogram is perpendicular to the z axis.

An event is registered if both crystals detect an annihilation photon within a coincidence time window $\tau$ (e.g., on the order of 4-5 ns), depending on the timing properties of the scintillator and the field of view. Aside from the effect of photon scatter, as discussed below, a pair of detectors is sensitive only to coincidence events originating in the volume between the two detectors, thereby eliminating the need for physical collimation, and thus significantly increasing sensitivity. Accurate corrections can be made for the self-absorption of photons within the patient (i.e., attenuation correction) so that accurate measurements of tracer concentration can be made.

The number of time coincidences detected per second within a field of view (FOV) of a detector is the count rate of the detector. The count rate at each of two oppositely disposed detectors, A and B, can be referred to as singles counts, or singles, $S_A$ and $S_B$. The time required for a gamma photon to travel from its point of origin to a point of detection is referred to as the time of flight, or TOF, of the gamma photon. TOF is dependent upon the speed of light c and the distance traveled. A time coincidence, or coincidence event, is identified if the time difference between the arrival of signals in a pair of oppositely disposed detectors is within the coincidence time window $\tau$. In conventional PET, the coincidence detection time window $\tau$ is wide enough so that an annihilation event occurring anywhere within the object would produce annihilation gamma photons reaching their respective detectors within the coincidence window. Coincidence time windows of 4.5-12 nsec are common for conventional PET, and are largely determined by the time resolution capabilities of the detectors and electronics.

As illustrated in FIG. 2, if an annihilation event occurs at the midpoint of a LOR, the TOF of the gamma photon detected in detector A ($T_A$) is equal to the TOF of the gamma photon detected in detector B ($T_B$). If an annihilation event occurs at a distance $\Delta x$ from the midpoint of the LOR, the difference between $T_A$ and $T_B$ is $\Delta t = 2\Delta x/c$, where c is the speed of light. If d is the distance between the detectors, the TOF difference $\Delta t$ could take any value from $-d/c$ to $+d/c$, depending on the location of the annihilation event.

In contrast to conventional PET, TOF-PET is based on recording the difference Δt between the detection times of the two gamma photons arising from the positron annihilation event in sub-intervals of the total coincidence window τ. This measurement allows the annihilation event to be localized along the LOR with a resolution of about 30-180 mm FWHM, assuming a time resolution of 200-1200 ps (picoseconds). Though less accurate than the spatial resolution of the scanner, this approximate localization is effective in reducing noise contributions both from random coincidence events and from scattered and unscattered photon coincidences that actually originated elsewhere in the object. This improves both the stability of the reconstruction and the signal-to-noise ratio (SNR) in the final image, especially when imaging large objects. TOF-PET may increase image SNR by a factor of 2 or more compared to conventional PET.

TOF scanners developed in the early 1980s were used for research and clinical applications, but the SNR gain provided by the TOF measurements of about 500 ps resolution was offset by poorer spatial resolution and lower sensitivity due to the low stopping power of the $BaF_2$ and CsF scintillation crystals used in such scanners. Consequently, those TOF systems could not compete successfully with conventional (non-TOF) BGO scanners. As a result, TOF-PET almost completely disappeared from the scene in the 1990s. Today, faster electronics and crystals such as LSO and $LaBr_3$ reopen the prospect of exploiting the TOF information without compromising other parameters such as the count rate, the sensitivity, and the energy and spatial resolutions.

Septumless or "3D" PET scanners (i.e., without interplane septa) currently constitute a large percentage of the total market for PET imaging. Because of the lack of interplane septa, scattered events (i.e., annihilation photons undergoing Compton scattering before reaching the detector) may represent a large portion of the measured data (e.g., up to 50% or more in clinical studies). An example of such scatter is shown in FIG. 3, which illustrates a septumless PET scanner utilizing a ring detector configuration, which is also applicable for use with the present invention.

An annihilation event occurring at emission point 21 produces two oppositely traveling gamma photons along LOR 22. One of the gamma photons, however, may undergo Compton scattering at scatter point 23, which changes its travel direction to path 24. Consequently, while the first gamma photon is detected by detector A in line with the originating LOR 22, the scattered gamma photon will be detected in detector B, rather than by detector C. Consequently, the coincidence event detected in detectors A and C will result in a false LOR 25 being identified, instead of the correct LOR 22.

An example of techniques to correct for such scattering in TOF PET utilizing a single scatter simulation (SSS) algorithm is disclosed in U.S. Pat. No. 7,397,035, the contents of which are incorporated herein by reference in entirety.

However, in reality, the scattering of gamma photons from annihilation events before reaching the detectors also includes multiple Compton scattering. For modern scanners with good energy resolution and a narrow photopeak energy window, recent Monte Carlo simulations have shown that only double scatter makes a significant contribution to the multiple scatter and higher order scatter contributions are very small or negligible.

Currently, only the single scatter component is accurately modeled, and multiple scatter is accounted for by scaling this model of single scatter to the measured data. This is problematic for several reasons, including the possibility that single and multiple scatter are distributed differently. Additionally, the regions of the data appropriate for use in such scaling can be difficult to identify, and the measured data in those regions are often too sparse or noisy to support an accurate scaling.

Therefore, there is a need for an improved scatter simulation method to accurately model single plus double scatter contributions to TOF-PET data for more accurate approximation of the total scatter contributions.

SUMMARY

The methods disclosed herein provide a physically complete, accurate, and absolutely scaled model for double scatter estimation in a PET scanner. Also disclosed herein is a novel sampling scheme for the double scatter integration that improves the efficiency of the calculation.

According to an aspect of the present disclosure, a computer-implemented method for applying scatter correction to a scan data acquired in a TOF PET scanner is disclosed. The method comprises: (A) selecting a pair of detector positions in the TOF PET scanner's detector ring; (B) numerically estimating the double scatter coincidence event rate of annihilation photons in the selected pair of detector positions, wherein the annihilation photons in a double scatter coincidence event are assumed to be scattered once, each photon by a different scatter point in the TOF PET scanner's image volume, during a TOF PET acquisition scan period; (C) selecting another pair of detector positions; (D) repeating step (B) wherein the selected pair of detector positions is the another pair of detector positions; (E) repeating steps (C) and (D) until all detector pairs of interest have been selected; and (F) scatter correcting acquired scan data obtained from the pair of detector positions during the TOF PET acquisition scan period to reconstruct a TOF PET image based on the scan data.

According to some embodiments, a method for applying scatter correction to a scan data acquired in a TOF PET scanner comprises: (A) selecting a pair of detector positions in the TOF PET scanner's detector ring; (B) numerically estimating the double scatter coincidence event rate of annihilation photons in the selected pair of detector positions, wherein one of the pair of annihilation photons in a double scatter coincidence event is assumed not to be scattered and the other of the two photons is scattered twice by a scatter point in the TOF PET scanner's image volume, during a TOF PET acquisition scan period; (C) selecting another pair of detector positions; (D) repeating step (B) wherein the pair of detector positions is the another pair of detector positions; and (E) repeating steps (C) and (D) until all detector pairs of interest have been selected; and (F) scatter correcting the acquired scan data obtained from the pair of detector positions during the TOF PET acquisition scan period to reconstruct a TOF PET image based on the scan data.

According to some embodiments, a system for processing and reconstructing TOF PET sinogram data is disclosed. The system comprises: a processor capable of executing instructions; and a non-transitory, machine readable storage medium encoded with program instructions for controlling a TOF PET scanner, such that when the processor executes the program instructions, the processor performs at least one of the disclosed methods for applying scatter correction to a scan data acquired in the TOF PET scanner.

Also disclosed is a non-transitory, machine readable storage medium encoded with program instructions for controlling a TOF PET scanner, such that when a processor executes the program instructions, the processor performs at least one of the disclosed methods for applying scatter correction to a scan data acquired in the TOF PET scanner.

BRIEF DESCRIPTION OF THE DRAWINGS

The invention will now be more fully described by way of example with reference to the accompanying drawings in which.

DETAILED DESCRIPTION

This description of the exemplary embodiments is intended to be read in connection with the accompanying drawings, which are to be considered part of the entire written description. The disclosed embodiments are merely exemplary of the invention and the invention may be embodied in various and alternative forms.

Disclosed herein is a new double scatter simulation (DSS) algorithm that, when combined with the previously known single scatter simulation (SSS) technique, accurately approximates the total Compton scattering contribution to PET data for both TOF and non-TOF PET scanning. These double scatter contributions are efficiently computed by considering a subset of pairs of the single scatter points. By fully accounting for the physics, an absolute scaling is achieved, reducing or eliminating the need for a sometimes problematic scaling to the emission data.

The DSS algorithm disclosed herein is predicated on the prior existence of an initial PET emission image (positron emissions/volume/time) of the person or object being scanned in the PET camera, and the corresponding image of the linear attenuation coefficients for the annihilation radiation within that person or object. This initial emission image may be uncorrected for scattered radiation, and thus inaccurate. The contribution of scattered radiation to this image, estimated by means of the SSS+DSS simulations, can be used to more accurately model the emission data, and thereby allow a more accurate reconstruction of the emission image. This process of scatter estimation followed by a corrected reconstruction can be iterated until the scattered radiation is fully accounted for.

Figure 4:
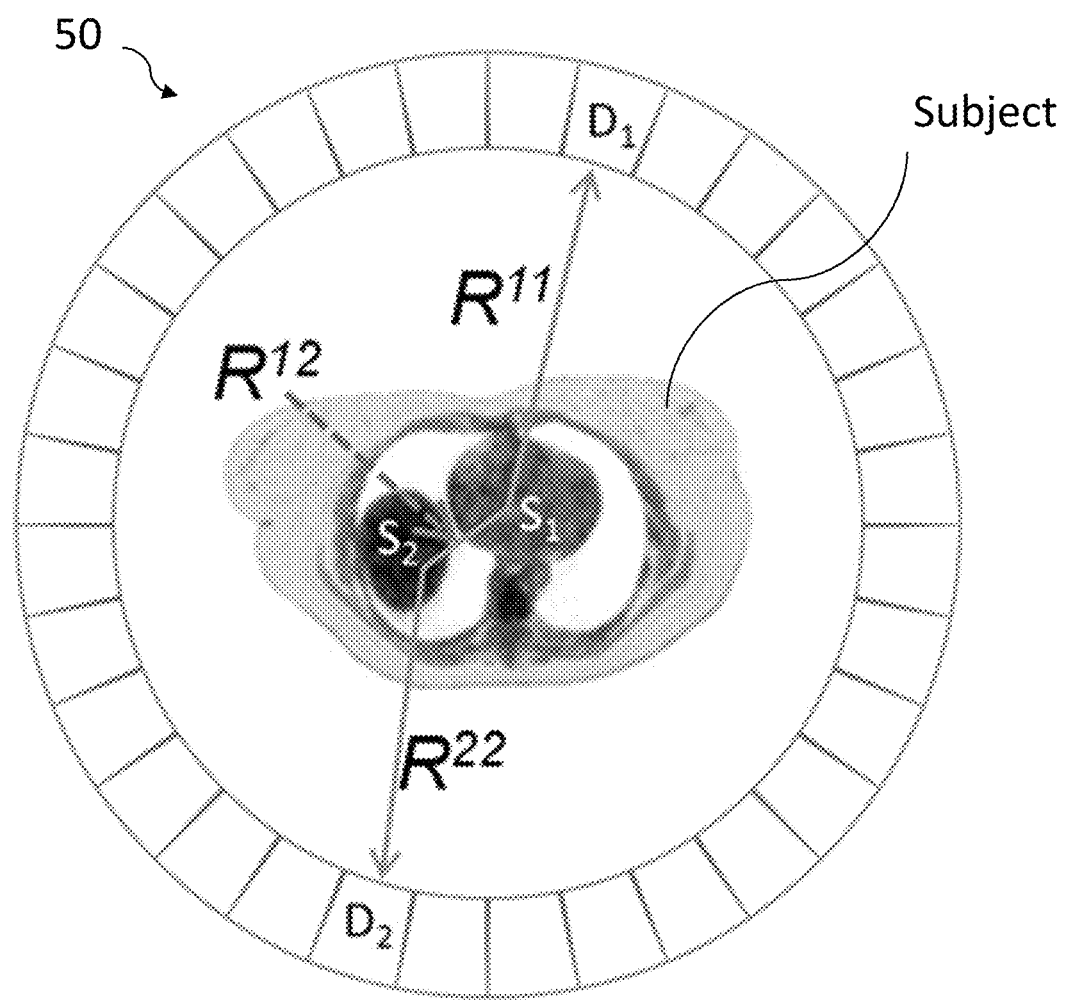
FIG. 4 is a diagram illustrating a possible trajectory for double scattering coincidence event with the three possible double scatter contributions to LOR ($D_1$, $D_2$) depending on the location of the emission source on the trajectory.

FIG. 4 shows a schematic illustration of a possible trajectory for the gamma photons from a double scattering coincidence event. $D_1$ and $D_2$ are detectors on a detector ring. $S_1$ and $S_2$ are possible scatter points. There are three distinct contributions, depending on the location of the emission point (the gamma annihilation point) relative to the two scatter points. For emission points on the rays ($S_1$, $D_1$) and ($S_2$, $D_2$) one photon will be unscattered and the other will be scattered twice. For emission points on the ray ($S_1$, $S_2$) both photons will be scattered once. According to an embodiment of the present disclosure, the total contribution from double scattering to the LOR ($D_1$, $D_2$) in a TOF offset bin n, from emission points along the ray $R^{11}$ between $S_1$ and $D_1$, is estimated as in the following equation (1):

$$R_n^{11} = \int\limits_{V_S}\int\limits_{V_S}\left[\int_{D_1}^{S_1} h_n[\Delta t(s)]n_e(s)ds\right]_1 \left[\frac{\sigma_{D_1}dV_{S_1}^{2/3}}{2\pi R_{S_1 D_1}^2}\right]_2 \quad (1)$$

$$\left[e^{\int_{D_1}^{S_1}\mu(E_0,s)ds}\right]_3 \left[\mu(E_0, S_1)dV_{S_1}^{1/3}\right]_4$$

-continued $$\left[\frac{1}{\sigma_c(E_0)}\frac{d\sigma_c(E_0,E_1)}{d\Omega}\right]_5 \left[\frac{dV_{S_2}^{2/3}}{R_{S_1S_2}^2}\right]_6$$

$$\left[e^{-\int_{S_1}^{S_2}\mu(E_1,s)ds}\right]_7 \left[\mu(E_1,S_2)dV_{S_2}^{1/3}\right]_8$$

$$\left[\frac{1}{\sigma_c(E_1)}\frac{d\sigma_c(E_1,E_{12})}{d\Omega}\right]_9 \left[\frac{\sigma_{D_2}}{R_{S_2D_2}^2}\right]_{10}$$

$$\left[e^{-\int_{S_2}^{D_2}\mu(E_{12},s)ds}\right]_{11} [\epsilon_{D_1}(E_0)\epsilon_{D_2}(E_{12})]_{12}$$

Only Compton scattering from free electrons, with total cross-section $\sigma_c$ and differential scattering cross-section $d\sigma_c/d\Omega$, is modeled. $E_0$ is the initial annihilation photon energy (511 keV). If $\theta_i$ is the scattering angle at $S_i$, the energy of a singly scattered photon is $E_i = E_0/(2-\cos\theta_i)$ and the energy of a doubly scattered photon is $E_{12}=E_0/(3-\cos\theta_1-\cos\theta_2)$. $E_{12}$ does not depend on the order of the two scatter events. There is a double volume integral over the two scatter points, and $dV_S$ is the incremental scattering volume. $n_e(s)$ is the emission rate density (annihilations/volume/time) at the spatial position s and $\mu(E, s)$ is the linear attenuation coefficient for energy E at s. $R_{SD}$ and $R_{SS}$ are the detector-scatter and scatter-scatter ray lengths, respectively. $\epsilon_D(E)$ is the detection efficiency at energy E, and $\sigma_D$ is the geometrical cross section of the detector. $\Delta t(s)$ is the coincidence detection time offset for two photons emitted from the points, which follow the double scatter trajectory. It is equal to their path length difference divided by the speed of light. $h_n[\ ]$ is an index function whose value is 1 if $\Delta t(s)$ falls in the $n^{th}$ discrete TOF offset bin, and 0 otherwise. The time resolution of the detectors is not modeled at this stage, but is applied after all contributions to the LOR $(D_1, D_2)$ have been computed. The number and widths of the discrete TOF offset bins may be chosen so that they fully cover the total coincidence window $\tau$. For the non-TOF case, there is only a single time bin to consider, which is the total coincidence window $\tau$, and the function $h_n[\ ]$ is always 1, so the time offsets $\Delta t(s)$ do not need to be computed.

Referring to the numbered brackets in equation (1), each numbered bracket being referred to as a term in the following discussion, Term 1 is the integral of emission density along $(D_1, S_1)$. Term 2 is the geometrical cross-section to intersect $D_1$ and $S_1$. Term 3 is the attenuation along $(D_1, S_1)$. Term 4 is the probability of interacting at the location $S_1$. Term 5 is the probability of Compton scatter toward $S_2$. Term 6 is the solid angle for scattering toward the location $S_2$. Term 7 is the attenuation along $(S_1, S_2)$. Term 8 is the probability of interacting at the location $S_2$. Term 9 is the probability of Compton scatter toward $D_2$. Term 10 is the solid angle for scattering toward $D_2$. Term 11 is the attenuation along $(S_1, D_2)$ or $(S_2, D_2)$. Term 12 is the detector efficiencies.

Referring to FIG. 4, in order to properly estimate the total double scatter contributions, we must also account for the other two distinct contribution sources mentioned above. The estimation of the contribution from the emission points on the ray $R^{22}$ between $S_2$ and $D_2$ is provided by the following equation (2):

$$R_n^{22} = \int_{V_S}\int_{V_\varepsilon}\left[\int_{D_2}^{S_2}h_n[\Delta t(s)]n_e(s)ds\right]_1 \left[\frac{\sigma_{D_2}dV_{S_2}^{2/3}}{2\pi R_{S_2D_2}^2}\right]_2 \quad (2)$$

$$\left[e^{-\int_{D_2}^{S_2}\mu(E_0,s)ds}\right]_3 \left[\mu(E_0,S_2)dV_{S_2}^{1/3}\right]_4$$

$$\left[\frac{1}{\sigma_c(E_0)}\frac{d\sigma_c(E_0,E_2)}{d\Omega}\right]_5 \left[\frac{dV_{S_1}^{2/3}}{R_{S_1S_2}^2}\right]_6$$

$$\left[e^{-\int_{S_2}^{S_1}\mu(E_2,s)ds}\right]_7 \left[\mu(E_2,S_1)dV_{S_1}^{1/3}\right]_8$$

$$\left[\frac{1}{\sigma_c(E_2)}\frac{d\sigma_c(E_2,E_{12})}{d\Omega}\right]_9 \left[\frac{\sigma_{D_1}}{R_{S_1D_1}^2}\right]_{10}$$

$$\left[e^{-\int_{S_1}^{D_1}\mu(E_{12},s)ds}\right]_{11} [\epsilon_{D_2}(E_0)\epsilon_{D_1}(E_{12})]_{12}$$

The estimation of the contribution from the emission points on the ray $R^{12}$ between $S_1$ and $S_2$, where the photons will each be scattered once, is provided by the following equation (3):

$$R_n^{12} = \int_{V_S}\int_{V_\varepsilon}\left[\int_{D_1}^{S_2}h_n[\Delta t(s)]n_e(s)ds\right]_1 \left[\frac{dV_{S_1}^{2/3}dV_{S_2}^{2/3}}{2\pi R_{S_1S_2}^2}\right]_2 \quad (3)$$

$$\left[e^{-\int_{S_1}^{S_2}\mu(E_0,s)ds}\right]_3 \left[\mu(E_0,S_1)dV_{S_1}^{1/3}\right]_4$$

$$\left[\frac{1}{\sigma_c(E_0)}\frac{d\sigma_c(E_0,E_1)}{d\Omega}\right]_5 \left[\frac{\sigma_{D_1}}{R_{S_1D_1}^2}\right]_6$$

$$\left[e^{-\int_{S_1}^{D_1}\mu(E_1,s)ds}\right]_7 \left[\mu(E_0,S_2)dV_{S_2}^{1/3}\right]_8$$

$$\left[\frac{1}{\sigma_c(E_0)}\frac{d\sigma_c(E_0,E_2)}{d\Omega}\right]_9 \left[\frac{\sigma_{D_2}}{R_{S_2D_2}^2}\right]_{10}$$

$$\left[e^{-\int_{S_2}^{D_2}\mu(E_2,s)ds}\right]_{11} [\epsilon_{D_1}(E_1)\epsilon_{D_2}(E_2)]_{12}$$

The total double scatter contribution to the LOR $(D_1, D_2)$ in a TOF offset bin n is obtained by summing together the partial estimates above: $R_n=R_n^{11}+R_n^{22}+R_n^{12}$, which has units of (number of counts)/cm²/sec. $R_n$ is the ideal TOF response. To account for the actual time resolution of the detectors, a discrete time resolution function, $p_{mn}$, is applied. $p_{mn}$ is the probability that an event actually occurring in time bin n would be measured by the detectors in time bin m. The measured TOF response in the LOR is therefore modeled as $R_m=\Sigma_n\,p_{mn}R_n$. The ideal and measured time bins may have different structures. For example, in the ideal case there may be many small bins, while the measured data may have fewer, wider time bins.

The integrals in equations (1)-(3) are computed by sampling scatter point positions, but the $1/R^2_{SS}$ factors in these equations suggest the contributions could become arbitrarily large when the two scatter points get close together, making it difficult to sample them adequately. This is dealt with by using an approximate analytical integration over a small volume $\Delta V_S$ around $S_1$ with a specified radius $R_S$ when $R_{SS}<R_S$. The possibility that $R_{SS}=0$ is allowed, in which case the scatter angle is chosen randomly. When the emission points lie between $S_1$ and $S_2$, there are three terms in equation (3) that involve the distance between $S_1$ and $S_2$, as shown in the first line in the set of equations (4) below. One needs to estimate the average value of these terms over all possible scatter point pairs lying in the sphere around $S_1$ with radius $R_S$. Instead of estimating this by discrete sampling, it is computed analytically using certain approximations. The second line follows from the first under the approximation that the emitter density $n_e$ and the linear attenuation coefficient $\mu$ do not vary significantly between $S_1$ and $S_2$. The third line is equivalent to the second, and the fourth line is equivalent to the third. The fifth line follows from the fourth under the assumption that the photon attenuation over a distance $R_S$ is small, and the desired average contribution is found to be $3n_e/R_s$. This value is used in place of sampled values of these terms whenever $R_{SS} < R_S$. In the TOF case, the TOF bins for the contributions are based on the positions of the sampled emission points as usual.

$$\left[\int_{S_1}^{S_2} n_e(s) ds\right] \left[\frac{1}{R_{S_1 S_2}^2}\right] \left[e^{-\int_{S_1}^{S_2} \mu(E_0,s) ds}\right] \approx$$

$$\frac{1}{\Delta V_s} \int_0^{R_s} \int_0^{\pi} \int_0^{2\pi} (n_e R) \left(\frac{1}{R^2}\right) (e^{-\mu R}) R^2 \sin\theta\, dR\, d\theta\, d\phi = \frac{4\pi n_e}{\Delta V_s} \int_0^{R_s} R e^{-\mu R} dR =$$

$$\frac{4\pi n_e}{\Delta V_s} \frac{1}{\mu(E_0)^2} [1 - e^{-\mu(E_0) R_s}(1 + \mu(E_0) R_s)] \approx \frac{4\pi n_e R_s^2}{\Delta V_s} = \frac{3 n_e}{R_s} \text{ for } \mu R_s \ll 1$$

When the emission points lie between $D_1$ and $S_1$ or $D_2$ and $S_2$, there are only two terms in equations (1) or (2) that involve the distance between $S_1$ and $S_2$, as shown in the first line in the set of equations (5) below. Following the same process as above, the desired average contribution is found to be $3/R_s^2$. This value is used in place of sampled values of these terms whenever $R_{SS} < R_S$.

$$\left[\frac{1}{R_{S_1 S_2}^2}\right] \left[e^{-\int_{S_1}^{S_2} \mu(E_1,s) ds}\right] \approx \frac{1}{\Delta V_s} \int_0^{R_s} \int_0^{\pi} \int_0^{2\pi} \left(\frac{1}{R^2}\right)(e^{-\mu R}) R^2 \sin\theta\, dR\, d\theta\, d\phi = \quad (5)$$

$$\frac{4\pi}{\Delta V_s} \int_0^{R_s} e^{-\mu R} dR =$$

$$\frac{4\pi}{\Delta V_s} \frac{1}{\mu(E_1)} [1 - e^{-\mu(E_1) R_s}] \approx \frac{4\pi R_s}{\Delta V_s} = \frac{3}{R_s^2} \text{ for } \mu R_s \ll 1$$

Figure 5:
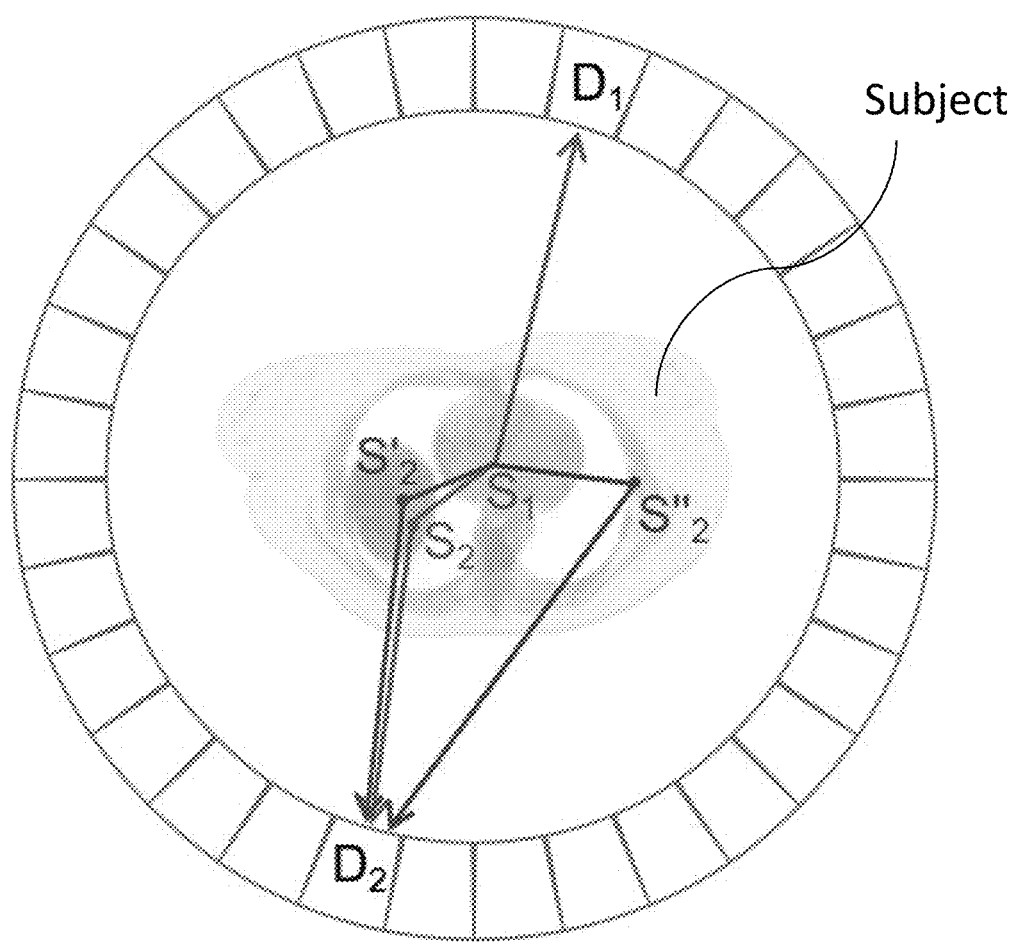
FIG. 5 is a diagram illustrating a possible first scatter point $S_1$ and three possible second scatter points, $S_2$, $S'_2$ and $S''_2$, defining 3 possible double scatter pair samples.

The integrals in equations (1)-(3) are computed by discrete sampling techniques. In particular, the volume integrals over $V_{S1}$ and $V_{S2}$ are discretized so that each volume element $dV_S$ is associated with one scatter point. For efficiency, the same set of scatter points used for single scatter estimation may be used for both double scatter points. In principle, for each $dV_{S1}$, all $dV_{S2}$ should be sampled. Therefore, for N scatter points, one should in principle compute contributions from all $N^2$ ordered pairs of scatter points (allowing for the possibility of 2 scatters within one $dV_S$ cell). In practice, however, complete sampling may not be practical or necessary. The pairs only need to adequately sample the different materials present, and scattering angles. Referring to FIG. 5, it can be seen that for a first scattering point $S_1$ some of the possible second scattering points, for example $S_2$ and $S'_2$, will give very similar contributions, while others, for example $S_2$ and $S''_2$, will give very different contributions. It is therefore advantageous for the efficiency of the simulation to choose a subset of the possible scatter point pairs that reduces the redundancy of the sampling without introducing significant bias.

To this end, a reduced sampling algorithm is used: Suppose there are N scatter points. Each scatter point has a randomly chosen position within a cell of a defined regular three-dimensional grid covering the imaging volume of interest. There is one scatter point per cell. Let M ($1 \leq M \leq N$) be a pair multiplicity such that each scatter point is to be associated with M other points to form M pairs per original point. The total number of scatter point pairs to be defined is thus NM. Define a super-grid having approximately $\sqrt{NM}$ super-cells. Each super-cell contains approximately $N/\sqrt{NM} = \sqrt{N/M}$ scatter points per grid cell. Each point belongs to one and only one cell. These $\sqrt{NM}$ cells are chosen to be contiguous and grouped so as to have minimal spatial extent. There are approximately $M \times \sqrt{N/M} = \sqrt{NM}$ pairs originating in each of the $\sqrt{NM}$ super-cells. For each super-cell, the second points per pair are chosen randomly subject to the constraint that all super-cells must be sampled, giving exhaustive sampling at the super-cell level. The scatter contributions computed using this reduced sampling are scaled up to account for the under-sampling. When $M \to N$, the super-cell is equal to a single scatter cell, and the sampling is exhaustive over all possible $N^2$ ordered pairs.

Figure 6:
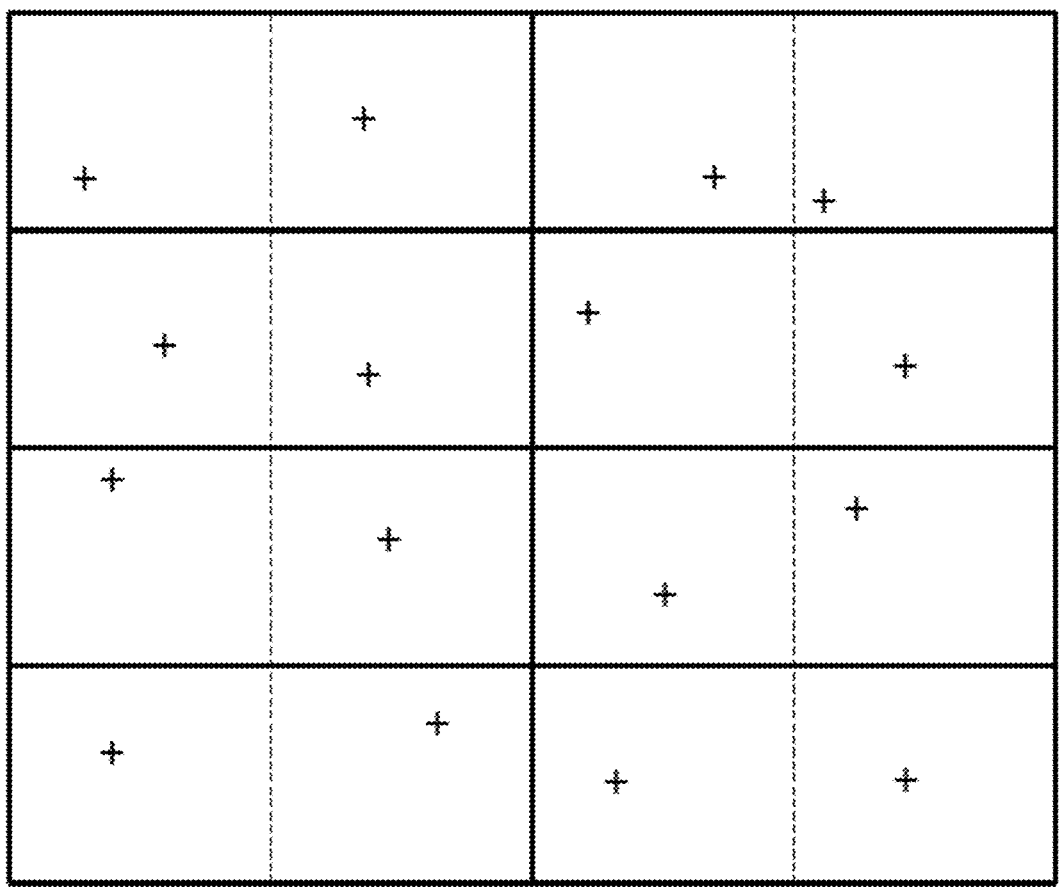
FIG. 6 is a diagram illustrating a supercell grid for N=16 and M=4.
Figure 7:
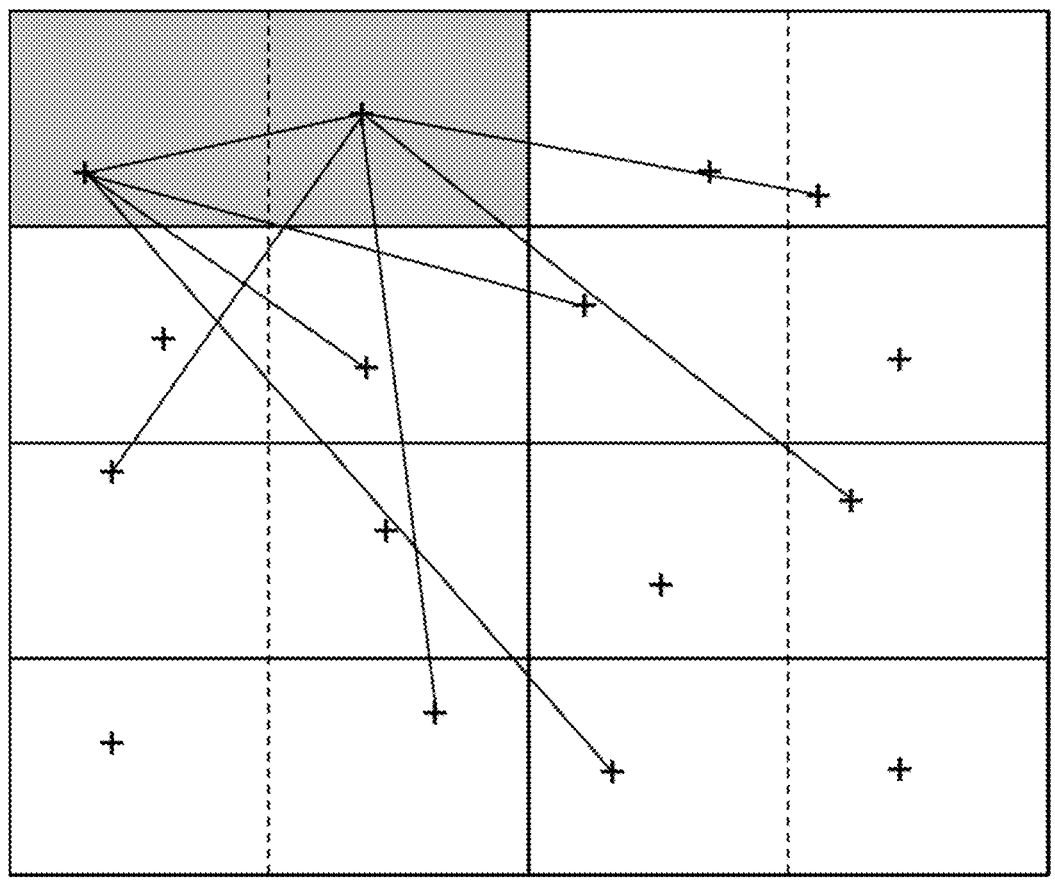
FIG. 7 is a diagram illustrating the 8 double scatter pairs associated with one supercell.
Figures 15A, 15B:
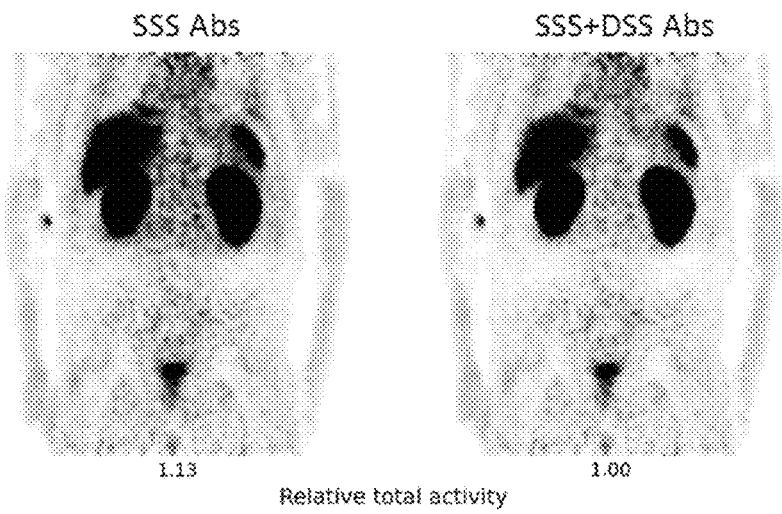
FIGS. 15A-15D are coronal images from two different reconstructions for each of two clinical PET studies using the radiotracer $^{68}$Ga-PSMA. The notations have the same meaning as in FIGS. 10A-10D.
Figures 15C, 15D:
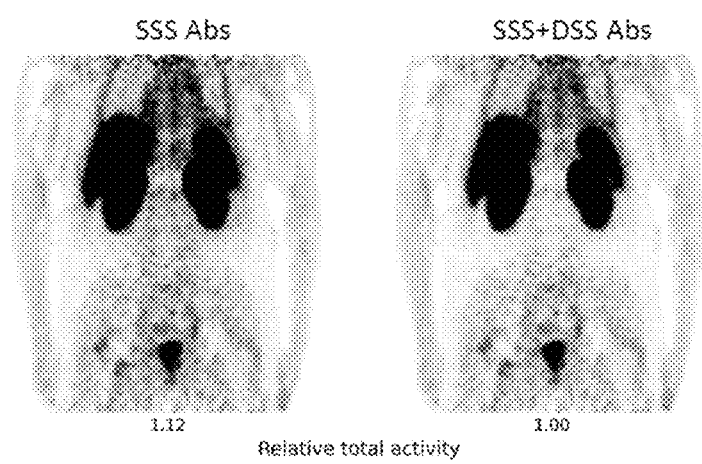

FIG. 6 shows an example of the scatter grid (dotted and solid lines) and super-grid (solid lines only), for the case N=16, and M=4. There are 16 scatter point cells and 8 super-cells, each containing 2 points. In FIG. 15, one of the super-cells is shaded, and 8 possible scatter point pairs associated with the two points in the super-cell are indicated. Out of the 256 possible scatter pairs in this example, only 64 will be sampled, but these are distributed with good spatial uniformity.

The DSS technique described herein can be efficiently implemented in conjunction with the SSS technique since they can share much of the same infrastructure, such as the scatter point distribution, detector sampling, detector to scatter point distances and angles, emission and attenuation ray sums, detector efficiencies, the time-of-flight resolution model, photon cross-section tables, and other components. To these common components, the DSS technique adds the scatter pair definition, ray sums between the scatter points, cross-sections for the second scatter, analytical approximations for contributions from closely spaced pairs, an efficient technique for sampling scatter pairs, and other components. Three new parameters are introduced to control the behavior of the DSS: a minimum energy for tracking a doubly scattered photon (e.g., 350 keV), the pair multiplicity M (e.g., 100), and the scatter point separation below which the analytical approximation is used (e.g., 2.5 cm).

DSS (like SSS) uses an "absolute scaling" technique to make its estimates of scatter quantitatively compatible with measured PET data. "Absolute scaling" means that a theoretically complete physical model for estimating scatter events/sec in a detector pair is used, as described in equations (1)-(3). But using this to directly estimate measured data would require a very accurate model of the detector efficiencies and count losses. However, the corresponding expression for unscattered events (below) involves similar efficiencies (last two terms):

$$T = \left[\int_{D_1}^{D_2} n_e(s) ds\right] \left[e^{-\int_{D_1}^{D_2} \mu(E_0,s) ds}\right] \left[\frac{\sigma_{D_1 D_2}^2}{2\pi R_{D_1 D_2}^2}\right] \epsilon_{D_1 D_2}^2(E_0)$$

The ratio of these efficiencies can be estimated much more accurately than the individual efficiencies, so these true coincidence efficiencies are estimated using the same physics models used for the scattered event efficiency calculations, and include in the SSS and DSS estimates:

$$e^{-\int_{D_1}^{D_2} \mu(E_0, s) ds} \int_{D_1}^{D_2} n_c(s) ds \sim \left( \left[ \frac{\sigma_{D_1 D_2}^2}{2\pi R_{D_1 D_2}^2} \right] \epsilon_{D_1 D_2}^2 (E_0) \right)^{-1} (S_1 + S_2) =$$

$$SSS + DSS$$

In other words, an estimated trues normalization is applied. This means that the sinogram computed by SSS+DSS is directly quantitatively ("absolutely") comparable to a normalized trues sinogram that represents the attenuated forward projection of the emission-rate density, with units of events/cm²/sec.

An initial validation of the DSS algorithm was performed by comparing it to Monte Carlo (MC) simulation of 20 and 30 cm diameter cylindrical water-filled phantoms, 26 cm long, uniformly activated with the positron-emitting isotope $^{18}$F. These MC simulations were performed with Penelope-2011 using a cylindrical geometry approximating the Siemens mMR PET/MR scanner (detector ring diameter 65.6 cm, axial FOV 26 cm). The calculations assumed an energy resolution of 13.5% at 511 keV and a photopeak energy window of 430-610 keV. These first results are for the non-TOF case. The DSS (and SSS) simulations are absolutely scaled—there is no cross-scaling to the MC results.

Figure 8:
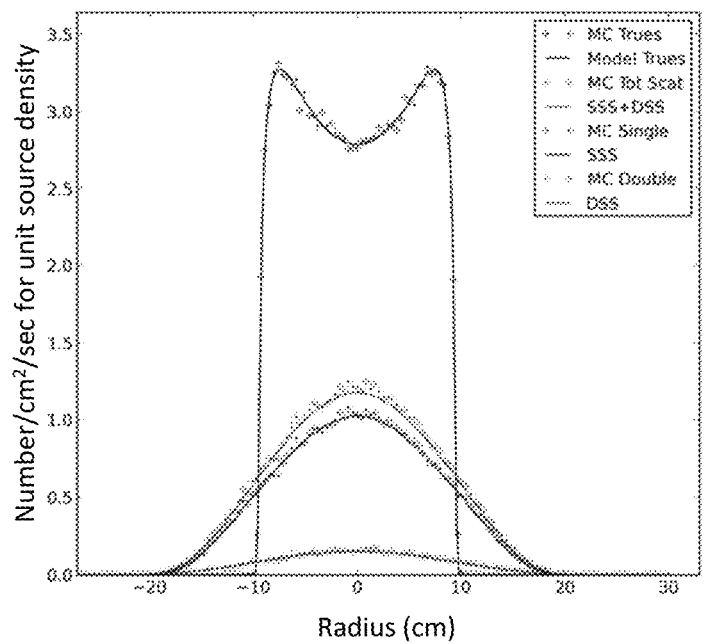
FIG. 8 is a plot of average sinogram radial profiles comparing validation data against Monte Carlo simulations for a 20 cm cylinder phantom.
Figure 9:
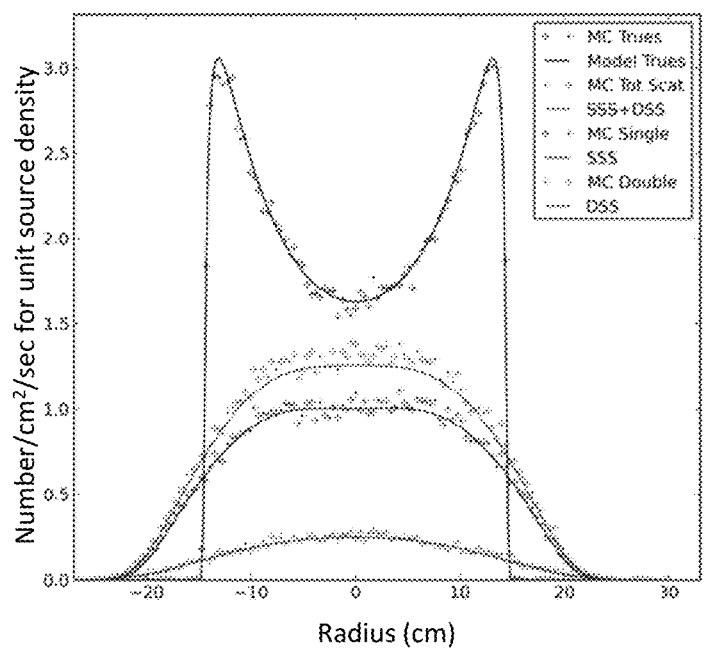
FIG. 9 is a plot of average sinogram radial profiles comparing validation data against Monte Carlo simulations for a 30 cm cylinder phantom.

FIG. 8 shows profiles for the MC, SSS and DSS sinogram estimates for the 20 cm phantom. These are radial profiles averaged over azimuthal and polar angles, and over z. The data labeled 'MC Trues' are unscattered events, and the curve labeled 'Model Trues' is a simple attenuated forward projection of the phantom. The data labeled 'MC Tot Scat' includes all scatter orders. The curve labeled 'SSS+DSS' is the result of the SSS and DSS simulations combined. The data labeled 'MC Single' includes only single scatter events. The curve labeled 'SSS' is the result of the SSS simulation. The data labeled 'MC Double' includes only double scatter events. The curve labeled 'DSS' is the result of the DSS simulation. FIG. 9 shows similar profiles for the 30 cm phantom simulation.

Table A reports the scatter fraction estimates resulting from the various simulations. The scatter fraction is defined as the ratio of the sum of the specified scattered events to the sum of all scattered and unscattered events from the MC simulation. Here $S_1$, $S_2$ and $S_{tot}$ are the MC single, double and total scatter fractions, respectively, and SSS and DSS refer to the single and double scatter fractions from the SSS and DSS algorithms.

These results show that the SSS and DSS simulations agree very well with the MC simulations, both in shape and in the relative magnitude of double and single scatter. The scatter fractions listed in Table A confirm that a single plus double scatter simulation can account for all but a few percent of the total scatter, suggesting that absolutely scaled SSS+DSS simulations could provide a viable clinical alternative to current rescaling algorithms.

TABLE A

| Scatter fractions | 20 cm | 30 cm |
| --- | --- | --- |
| MC $S_1$ | 25.5% | 30.9% |
| SSS | 25.1 ± .24% | 30.7 ± .12% |
| MC $S_2$ | 4.05% | 6.96% |
| DSS | 4.05 ± .20% | 6.80 ± .17% |
| MC $S_{tot}$ | 30.0% | 38.9% |
| MC ($S_1 + S_2$) | 29.6% | 37.9% |
| SSS + DSS | 29.1% | 37.4% |
| MC ($S_1 + S_2$)/$S_{tot}$ | 0.99 | 0.97 |
| (SSS + DSS)/$S_{tot}$ | 0.97 | 0.96 |

Figure 17:
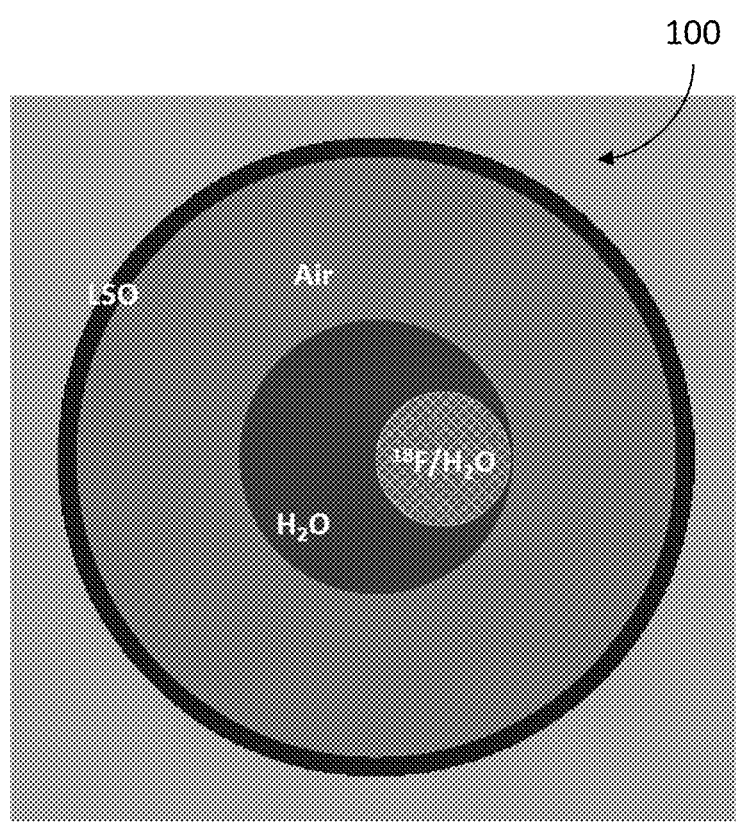
FIG. 17 is a schematic illustration of a transaxial slice of the simulated phantom.

A similar validation of DSS versus MC was performed for simulations that included time-of-flight (TOF) discrimination. In this case, the simulated phantom 100, as shown in cross-section in FIG. 17 consisted of a 30 cm diameter and 26 cm long water-filled cylinder, in which a 14 cm diameter by 26 cm long region, offset by 7.5 cm from the center, was activated with $^{18}$F. The same detector ring diameter, and photopeak energy window, were used as previously, but in this case the energy resolution was set to 10%. A TOF resolution of 0.1 ns was assumed and 11 TOF bins each 0.2 ns wide were modeled.

Figure 18A:
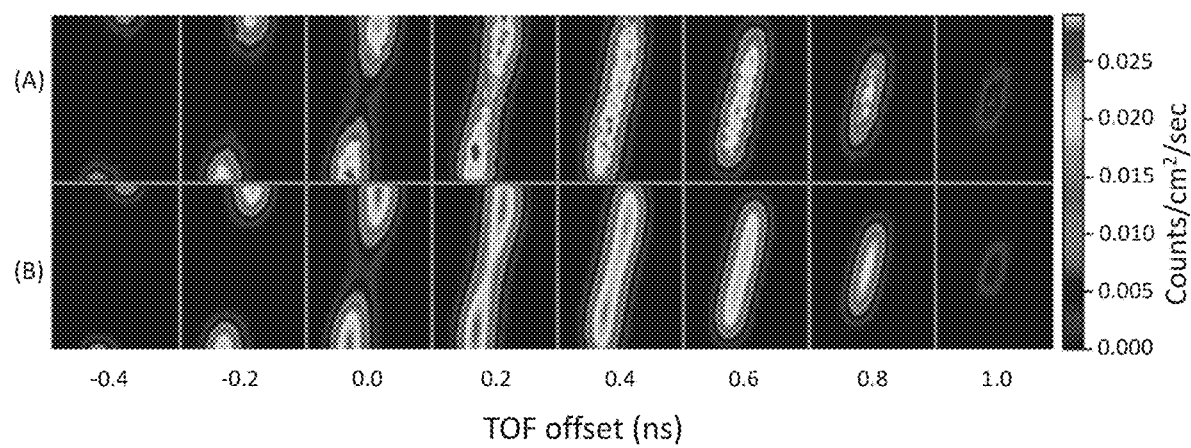
FIG. 18A shows a comparison of Monte Carlo simulation double scatter TOF sinograms to the corresponding DSS TOF sinograms for 8 TOF bins with significant data.
Figure 18B:
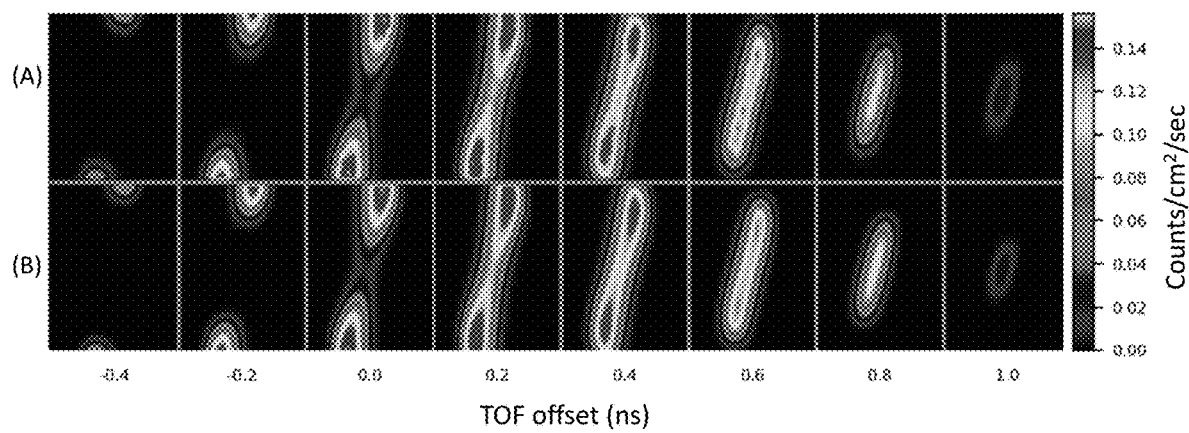
FIG. 18B show a comparison of Monte Carlo simulation total scatter (all orders) TOF sinograms to the corresponding SSS+DSS TOF sinograms.

FIG. 18A compares the MC double scatter TOF sinograms to the corresponding DSS TOF sinograms, for the 8 TOF bins with significant data. In FIG. 18A, the row (A) are the MC double scatter sinograms and row (B) are the DSS TOF sinograms. FIG. 18B compares the MC total scatter (all orders) sinograms to the corresponding SSS+DSS TOF sinograms, for the 8 TOF bins with significant data. In FIG. 18B, the row (A) are the MC total scatter sinograms and row (B) are the SSS+DSS sinograms. These sinograms represent averages over polar angle and z position. Table B gives the ratio of the sums over these sinograms, as well as the ratio of their total over all TOF bins (non-TOF). The numbers in parentheses are the standard deviations of the ratios over 10 repeat SSS and DSS simulations. The good absolute agreement between the MC and SSS+DSS simulations confirms that the TOF SSS and DSS algorithms give an adequate representation of the physics of scattering in TOF PET, and further show that absolute SSS+DSS only slightly underestimates the total scatter.

TABLE B

| TOF offset (ns) | DSS/MC double | SSS + DSS/MC total |
| --- | --- | --- |
| −0.4 | 0.873 (0.036) | 0.853 (0.011) |
| −0.2 | 1.008 (0.024) | 0.971 (0.007) |
| 0.0 | 1.014 (0.019) | 0.985 (0.005) |
| 0.2 | 1.045 (0.018) | 1.003 (0.006) |
| 0.4 | 1.038 (0.017) | 0.999 (0.005) |
| 0.6 | 1.027 (0.014) | 0.982 (0.004) |
| 0.8 | 1.018 (0.020) | 0.953 (0.007) |
| 1.0 | 0.729 (0.031) | 0.689 (0.014) |
| non-TOF | 1.023 (0.015) | 0.983 (0.005) |

Several tests of the DSS algorithm on clinical data were performed for the non-TOF case, to evaluate its effectiveness and robustness. FIGS. 10A-10D are coronal images from four different reconstructions of clinical PET data using the radiotracer $^{18}$F-DCFPyL. They show that the absolutely scaled SSS+DSS technique results in images that are arguably superior visually and quantitatively to the other reconstruction options.

Figures 10A, 10B, 10C, 10D:
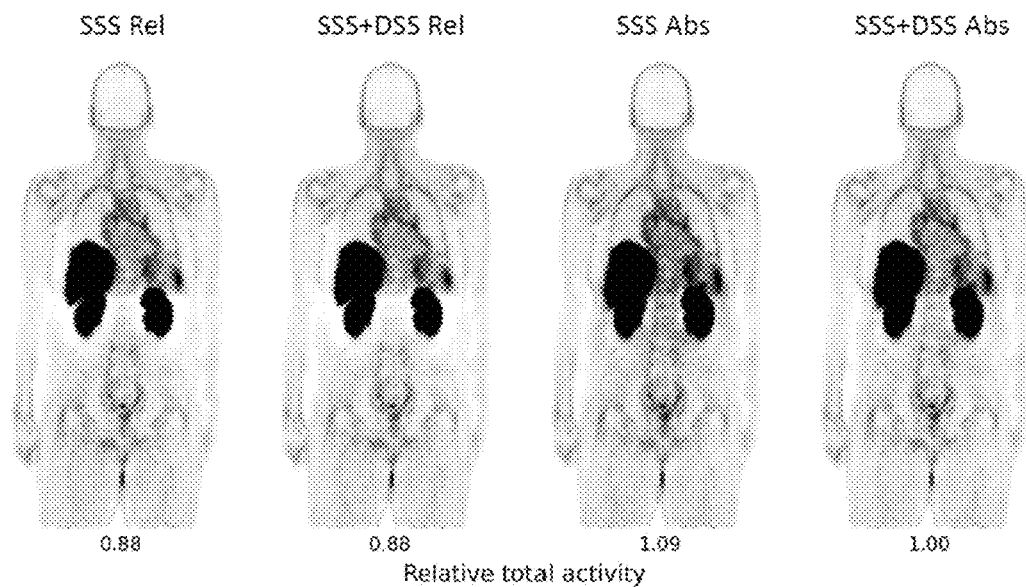
FIGS. 10A-10D are coronal images from four different reconstructions of clinical PET data using the radiotracer $^{18}$F-DCFPyL. 'SSS'=single scatter simulation, 'DSS'=double scatter simulation, 'Rel'=relative scaling, 'Abs'=absolute scaling. 'Relative total activity' refers to the total activity in the imaged portion of the body compared to the 'SSS+DSS Abs' case.
Figures 11A, 11B, 11C:
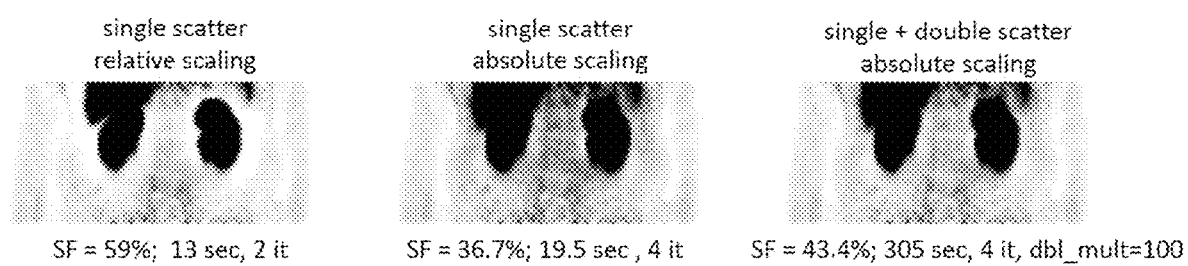
FIGS. 11A-11C are coronal images from three different reconstructions of clinical PET data using the radiotracer $^{18}$F-DCFPyL (same patient as in FIGS. 10A-10D). 'SF'=scatter fraction, 'it'=number of iterations used in the reconstruction, 'sec'=seconds required for the reconstruction, 'dbl_mult'=multiplicity factor used for selecting double scatter points.
Figures 12A, 12B, 12C, 12D:
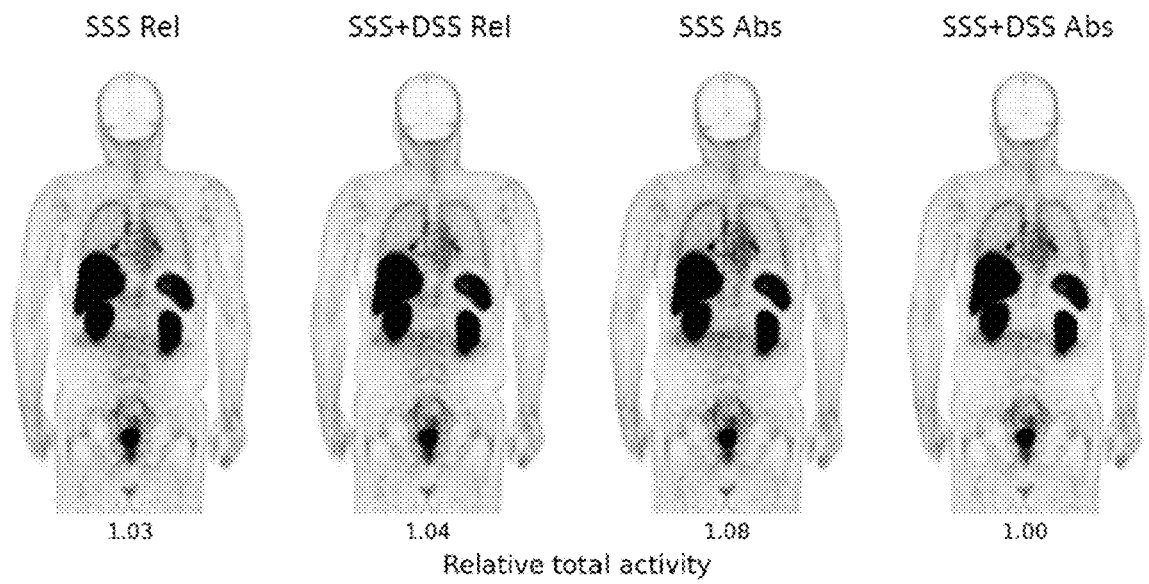
FIGS. 12A-12D are coronal images from four different reconstructions of a second clinical PET study using the radiotracer $^{18}$F-DCFPyL. The notations have the same meaning as in FIGS. 10A-10D.

FIGS. 11A-11C are zoomed image sections from three of the reconstructions shown in FIGS. 10A, 10C, and 10D, respectively, showing that the SSS+DSS Abs algorithm gives intermediate results for scatter fractions compared to the two algorithms currently available in clinical reconstruction software.

FIGS. 12A-12D are coronal images from four different reconstructions of a second clinical PET study using the radiotracer $^{18}$F-DCFPyL, showing that the SSS+DSS Abs images are comparable to those produced by the other reconstruction options.

Figures 13A, 13B, 13C:
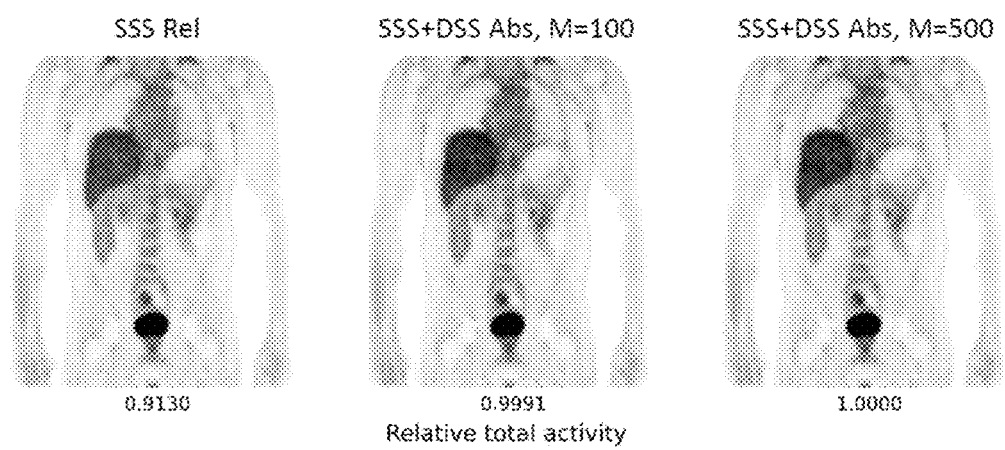
FIGS. 13A-13C are coronal images from three different reconstructions of a clinical PET study using the radiotracer $^{18}$F-FDG. The notations have the same meaning as in FIGS. 10A-10D. 'M'=the multiplicity factor used for selecting double scatter points.
Figures 14A, 14B:
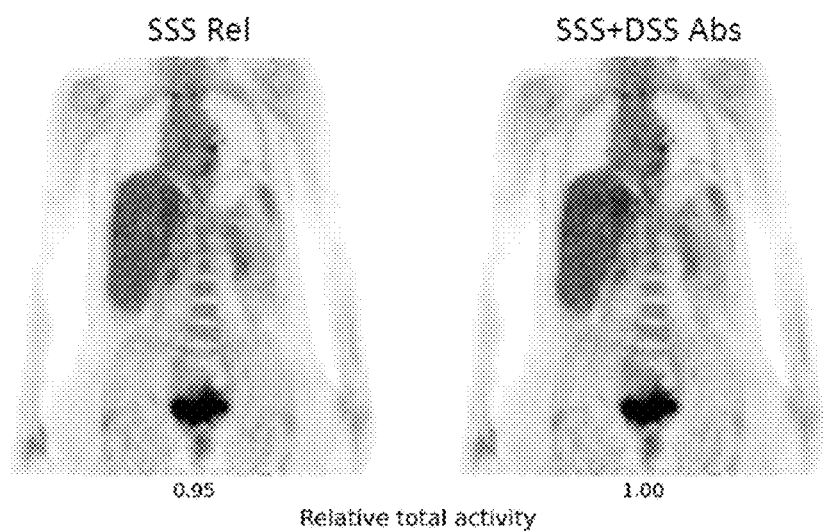
FIGS. 14A-14D are coronal images from two different reconstructions for each of two clinical PET studies using the radiotracer $^{18}$F-FDG. The notations have the same meaning as in FIGS. 10A-10D.
Figures 14C, 14D:
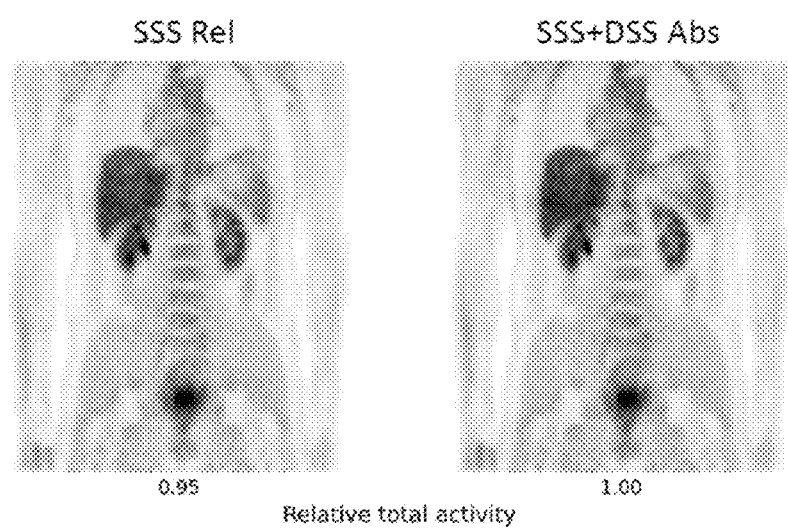

FIGS. 13A-13C are coronal images from three different reconstructions of a clinical PET study using the radiotracer $^{18}$F-FDG. It is found that increasing the double scatter pair multiplicity factor M from 100 to 500 has very little effect on the image. This indicates the large values of M, which entail longer reconstruction times, will not be necessary.

FIGS. 14A-14D are coronal images from two different reconstructions for each of two clinical PET studies using the radiotracer $^{18}$F-FDG, showing that in these cases SSS+DSS Abs gives comparable results to the current standard reconstruction SSS Rel.

FIGS. 15A-15D are coronal images from two different reconstructions for each of two clinical PET studies using the radiotracer $^{68}$Ga-PSMA. They show that reconstructions using SSS+DSS Abs result in higher, and probably more accurate, estimates of the scatter fraction than the current clinical standard reconstruction for this type of study, SSS Abs, which is known to underestimate the total scatter.

Figures 16A, 16B:
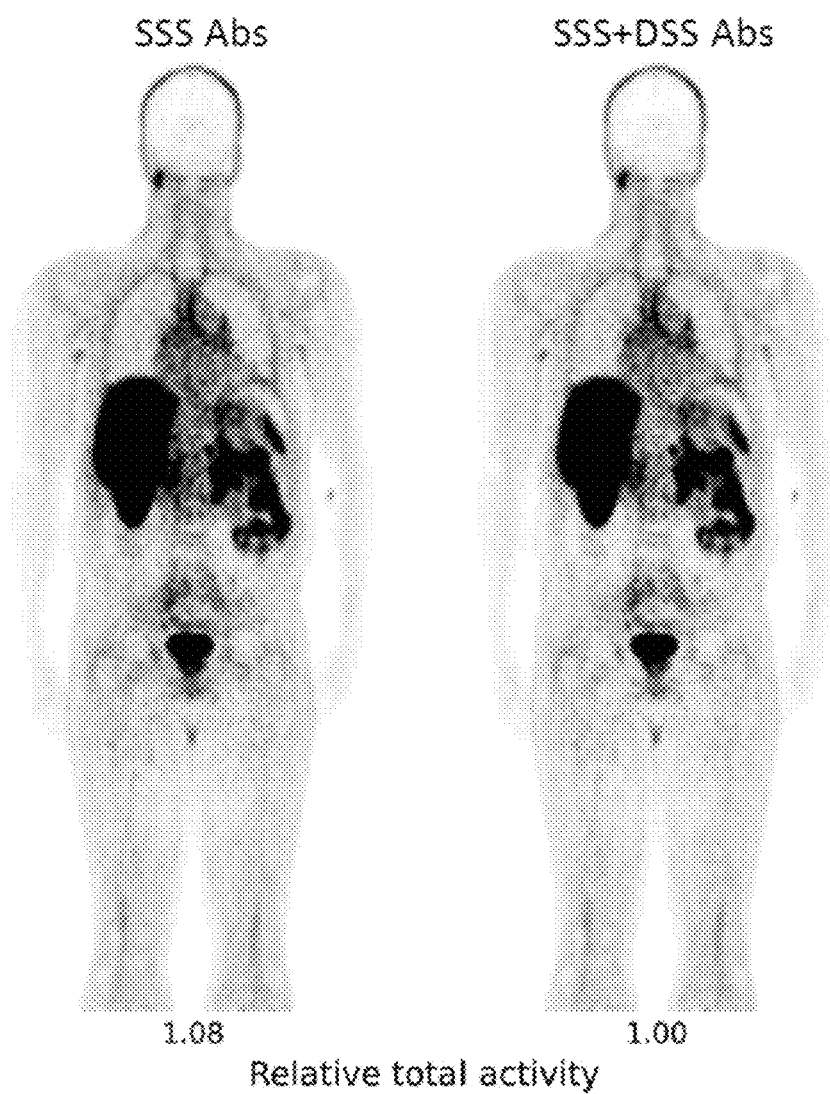
FIGS. 16A-16B are coronal images from two different reconstructions of a clinical PET study using the radiotracer $^{68}$Ga-PSMA. The notations have the same meaning as in FIGS. 10A-10D.

FIGS. 16A-16B are coronal images from two different reconstructions of a second clinical PET study using the radiotracer $^{68}$Ga-PSMA. Again, they show that SSS+DSS Abs produces less underestimation of the total scatter than the standard SSS Abs technique, because it includes double as well as single scatter.

Applying the DSS technique described above, methods for scatter correction in a TOF PET scanner will be described. It is to be understood that non-TOF DSS is included as a special case of TOF DSS.

[Double Single Scatter Estimation]—

In some embodiments, a method for applying scatter correction to a scan data acquired in a time-of-flight positron emission tomography (TOF PET) scanner assuming that both photons in the pairs of annihilation photons are scattered once is disclosed. The method comprises:

(A) selecting a pair of detector positions in the TOF PET scanner's detector ring;

(B) numerically estimating the double scatter coincidence event rate of annihilation photons in the selected pair of detector positions, wherein the annihilation photons in a double scatter coincidence event are assumed to be scattered once, each photon by a different scatter point in the TOF PET scanner's image volume, during a TOF PET acquisition scan period;

(C) selecting another pair of detector positions;

(D) repeating step (B) wherein the selected pair of detector positions is the another pair of detector positions;

(E) repeating steps (C) and (D) until all detector pairs of interest have been selected; and (F) scatter correcting, or modeling scatter in, the acquired scan data obtained from the pair of detector positions during the TOF PET acquisition scan period to reconstruct a TOF PET image based on the scan data.

Referring to equation (3), in some embodiments of the method, the selected pair of detector positions are $D_1$ and $D_2$, and the numerically estimating step comprises:

a) selecting the two scatter points, $S_1$ and $S_2$, in the TOF PET scanner's image volume;

b) sampling values of the emission rate density between the two scatter points $S_1$ and $S_2$, determining the time of flight offset bin, n, for each contribution, and storing these values in a vector $R_n^{12}$; [Term 1 in (3)]

c) calculating an exponential function of the negative of the line integral of the linear attenuation coefficients at energy $E_0$ between the two scatter points $S_1$ and $S_2$; [Term 3 in (3)]

d) calculating the exponential function of the negative of the line integral of the linear attenuation coefficients at energy $E_1$ between $S_1$ and $D_1$; [Term 7 in (3)]

e) calculating the exponential function of the negative of the line integral of the linear attenuation coefficients at energy $E_2$ between $S_2$ and $D_2$; [Term 11 in (3)]

f) calculating the reciprocals of the squares of the distances from $S_1$ to $S_2$, from $S_1$ to $D_1$, and from $S_2$ to $D_2$; [Terms 2, 6 and 10 in (3)]

g) calculating the linear attenuation coefficients at energy $E_0$, at the points $S_1$ and $S_2$; [Terms 4 and 8 in (3)]

h) calculating the ratio of the differential Compton cross section for a photon at energy $E_0$ to scatter to an energy $E_1$ to its total Compton cross section; [Term 5 in (3)]

i) calculating the ratio of the differential Compton cross section for a photon at energy $E_0$ to scatter to an energy $E_2$ to its total Compton cross section; [Term 9 in (3)]

j) calculating the geometrical cross section of detector $D_1$ for the photon traveling from $S_1$; [Term 6 in (3)]

k) calculating the geometrical cross section of detector $D_2$ for the photon traveling from $S_2$; [Term 10 in (3)]

l) calculating the detection efficiency of detector $D_1$ for the photon traveling from $S_1$ with energy $E_1$; [Term 12 in (3)]

m) calculating the detection efficiency of detector $D_2$ for the photon traveling from $S_2$ with energy $E_2$; [Term 12 in (3)]

n) calculating the image sample volumes associated with $S_1$ and with $S_2$; [Terms 2, 4 and 8 in (3)]

o) multiplying the quantities computed in b) through n) together to get one contribution to the double scatter count rate for the detector pair $D_1$, $D_2$, for each sampled time of flight offset bin in $R_n^{12}$;

p) selecting another pair of distinct scatter points $S_1$ and $S_2$, repeating steps a) through o) and adding the results to the previous results in $R_n^{12}$;

q) repeating step p) until the entire image volume has been adequately sampled by both $S_1$ and $S_2$.

In some embodiments of the method, the computed line integrals, Compton cross sections, geometrical cross sections, detector efficiencies, and scatter point positions can be cached for reuse.

In some embodiments of the method, each scatter point is chosen randomly within a cell of a regular spatial grid, one point per cell. Here, 'regular spatial grid' refers to a three-dimensional rectilinear grid having uniform cell size. In some embodiments, a subset of all possible scatter point pairs is used for the calculation.

[Single Double Scatter Estimation Case]—

In some embodiments, a method for applying scatter correction to a scan data acquired in a time-of-flight positron emission tomography (TOF PET) scanner assuming that one of the two photons in the pairs of annihilation photons is scattered twice and the other of the two photons is not scattered is disclosed. The method comprises:

(AA) selecting a pair of detector positions in the TOF PET scanner's detector ring;

(BB) numerically estimating the double scatter coincidence event rate of annihilation photons in the selected pair of detector positions, wherein one of the pair of annihilation photons in a double scatter coincidence event is assumed not to be scattered and the other of the two photons is scattered twice, once at each of two scatter points in the TOF PET scanner's image volume, during a TOF PET acquisition scan period;

(CC) selecting another pair of detector positions;

(DD) repeating step (BB) wherein the pair of detector positions is the another pair of detector positions;

(EE) repeating steps (CC) and (DD) until all detector pairs of interest have been selected; and (FF) scatter correcting, or modeling scatter in, the acquired scan data obtained from the pair of detector positions during the TOF PET acquisition scan period to reconstruct a TOF PET image based on the scan data.

Referring to equation (1), in some embodiments of the method, the selected pair of detector positions are $D_1$ and $D_2$ and the step (BB) comprises:

aa) selecting the two scatter points $S_1$ and $S_2$ in the TOF PET scanner's image volume;

bb) sampling values of the emission rate density between $D_1$ and $S_1$, determining the time of flight offset bin, n, for each sample, and storing these values in a vector quantity $R_n^{11}$; [Term 1 in (1) or (2)]

cc) calculating an exponential function of the negative of the line integral of the linear attenuation coefficients at energy $E_0$ between $D_1$ and $S_1$; [Term 3 in (1) or (2)]

dd) calculating the exponential function of the negative of the line integral of the linear attenuation coefficients at energy $E_1$ between $S_1$ and $S_2$; [Term 7 in (1) or (2)]

ee) calculating the exponential function of the negative of the line integral of the linear attenuation coefficients at energy $E_{12}$ between $S_2$ and $D_2$; [Term 11 in (1) or (2)]

ff) calculating the reciprocals of the squares of the distances from $S_1$ to $S_2$, from $S_1$ to $D_1$, and from $S_2$ to $D_2$; [Terms 2, 6 and 10 in (1) or (2)]

gg) calculating the linear attenuation coefficients for energy $E_0$ at $S_1$ and for $E_1$ at $S_2$; [Terms 4 and 8 in (1) or (2)]

hh) calculating the ratio of the differential Compton cross section for a photon at energy $E_0$ to scatter to an energy $E_1$ to its total Compton cross section; [Term 5 in (1) or (2)]

ii) calculating the ratio of the differential Compton cross section for a photon at energy $E_1$ to scatter to an energy $E_{12}$ to its total Compton cross section; [Term 9 in (1) or (2)]

jj) calculating the geometrical cross section of detector $D_1$ for a photon pair produced between $D_1$ and $S_1$; [Term 6 in (1) or (2)]

kk) calculating the geometrical cross section of detector $D_2$ for the photon traveling from $S_2$; [Term 10 in (1) or (2)]

ll) calculating the detection efficiency of detector $D_1$ for the photon traveling from the emission point with energy $E_0$; [Term 12 in (1) or (2)]

mm) calculating the detection efficiency of detector $D_2$ for the photon traveling from $S_2$ with energy $E_{12}$; [Term 12 in (1) or (2)]

nn) calculating the image sample volumes associated with $S_1$ and with $S_2$; [Terms 2, 4, 6 and 8 in (1) or (2)]

oo) multiplying the quantities computed in bb) through nn) together to get one contribution to the double scatter count rate for the detector pair $D_1$, $D_2$, for each sampled time of flight offset bin in $R_n^{11}$;

pp) selecting another pair of distinct scatter points $S_1$ and $S_2$, repeating steps aa) through oo) and add the results to the previous results in $R_n^{11}$; and qq) repeating step pp) until the entire image volume has been adequately sampled by both $S_1$ and $S_2$.

In some embodiments of the method, the computed line integrals, Compton cross sections, geometrical cross sections, detector efficiencies, and scatter point positions can be cached for reuse. In some embodiments of the method, each scatter point is chosen randomly within a cell of a regular spatial grid, one point per cell. In some embodiments, a subset of all possible scatter point pairs is used for the calculation.

Referring to equation (2) instead of (1), in some embodiments of the method comprising the steps (AA), (BB), and (CC) described above, for the case that the annihilation photons are emitted between $D_2$ and $S_2$, the step (BB) can comprise the steps aa) through qq) described above but with the following substitutions of the variables: $D_1 \leftrightarrow D_2$, $S_1 \leftrightarrow S_2$, $E_1 \rightarrow E_2$, and $R_n^{11} \rightarrow R_n^{22}$. In some embodiments of the method, the computed line integrals, Compton cross sections, geographical cross sections, detector efficiencies and scatter point positions can be cached for reuse. In some embodiments of the method, each scatter point is chosen randomly within a cell of a regular spatial grid, one point per cell. In some embodiments of the method, a subset of all possible scatter point pairs is used for the calculation.

In some embodiments of the method, the total double scatter contribution for each detector pair of interest is computed as: $R_n = R_n^{11} + R_n^{22} + R_n^{12}$. In some embodiments of the method, a discrete detector time resolution function, $p_{mn}$, is applied according to $R_m = \Sigma_n p_{mn} R_n$, to estimate the probability that an event actually occurring in time bin n would be measured by the detectors in time bin m.

According to another aspect of the present disclosure, a method for applying scatter correction to a scan data acquired in a TOF PET scanner comprises (I) calculating the time of flight offset distribution of two detected photons in double scatter coincidence events; and (II) scatter correcting acquired scan data obtained during the TOF PET acquisition scan period to reconstruct a TOF PET image based on the scan data. In some embodiments, the step (I) can comprise:

a) selecting two detector positions $D_1$ and $D_2$ in the TOF PET scanner's detector ring, defining them so that $D_1$ is in the positive time offset direction;

b) creating a time offset array initialized to zero;

c) selecting two scatter points in the image volume, thereby defining a double scatter path;

d) for each point sampled in the discrete line integrals of the emission rate density along the segments of the double scatter path, computing (1) the distance $d_1$ along the double scatter path from the emission point to $D_1$, (2) the distance $d_2$ along the double scatter path from the emission point to $D_2$, and (3) the contribution to the detector response from the emission rate density at this emission point;

e) computing the time of flight offset as $t=(d_2-d_1)/c$, where c is the speed of light;

f) adding the contribution to the double scatter count rate in ($D_1$, $D_2$) from this emission point into the bin of the time offset array corresponding to t;

g) repeating steps c) through f) until all scatter point pairs have been adequately sampled;

h) recording the values of the time offset array in the double scatter sinogram, in the appropriate time of flight bins for the detector pair ($D_1$, $D_2$); and i) repeating steps a) through h) for all detector pairs represented in the sinogram. In some embodiments of the method, the data in the time offset array are convolved with a time resolution function before being recorded.

According to another aspect of the present disclosure, a method for applying scatter correction to a scan data acquired in a time-of-flight positron emission tomography (TOF PET) scanner is disclosed. The method comprises estimating contributions from annihilation photons from double scatter coincidence events arising from two scatter points $S_1$ and $S_2$ when the two scatter points lie close together; and scatter correcting acquired scan data obtained from a pair of detector positions during the TOF PET acquisition scan period to reconstruct a TOF PET image based on the scan data.

In some embodiments of the method, the estimating step comprises: defining a minimum distance $R_s$ between the two scatter points $S_1$ and $S_2$; and when the distance between $S_1$ and $S_2$ is less than $R_s$, using an analytical calculation of the average contribution from certain terms in the expressions for the double scatter event rates. These are terms 1, 2 and 3 in equation (3); and terms 6 and 7 in equations (1) and (2).

In some embodiments of the method, for the case that both photons are scattered once, the three terms 1, 2 and 3 in equation (3) that involve the distance between the scatter points are replaced by the quantity $3n_e/R_s$, where $n_e$ is the average emitter rate density at the scatter points.

In some embodiments of the method, for the case that one photon is scattered twice and the other is not scattered, the two terms 6 and 7 in equations (1) and (2) that involve the distance between the scatter points are replace by the quantity $3/R_s^2$.

According to some embodiments, a method for applying scatter correction to a scan data acquired in a TOF PET scanner is disclosed. The method comprises: selecting a set of double scatter point pairs that contribute to double scattering of annihilation photons; and scatter correcting the acquired scan data to reconstruct a TOF PET image based on the scan data.

In the various embodiments of the method, the step of selecting a set of double scatter point pairs that contribute to double scattering of annihilation photons comprises:

a) defining a set of N single scatter points in the reconstructed PET images from which the double scatter contribution is to be computed;

b) defining a pair multiplicity factor M which is between 1 and N;

c) defining a grid in the images having approximately $\sqrt{NM}$ cells, with approximately $\sqrt{N/M}$ scatter points per cell, each point belonging to one and only one cell; and d) forming NM scatter point pairs by randomly choosing scatter points subject to the constraint that the scatter point pairs sample all cell pairs exhaustively. In some embodiments of the method, the N single scatter points are uniformly distributed over the entire volume of the images. In some embodiments of the method, the N single scatter points are randomly distributed over the entire volume of the images. In some embodiments of the method, the grid is a uniform rectilinear grid with a constant cell size, covering the entire volume of the images.

Figure 1:
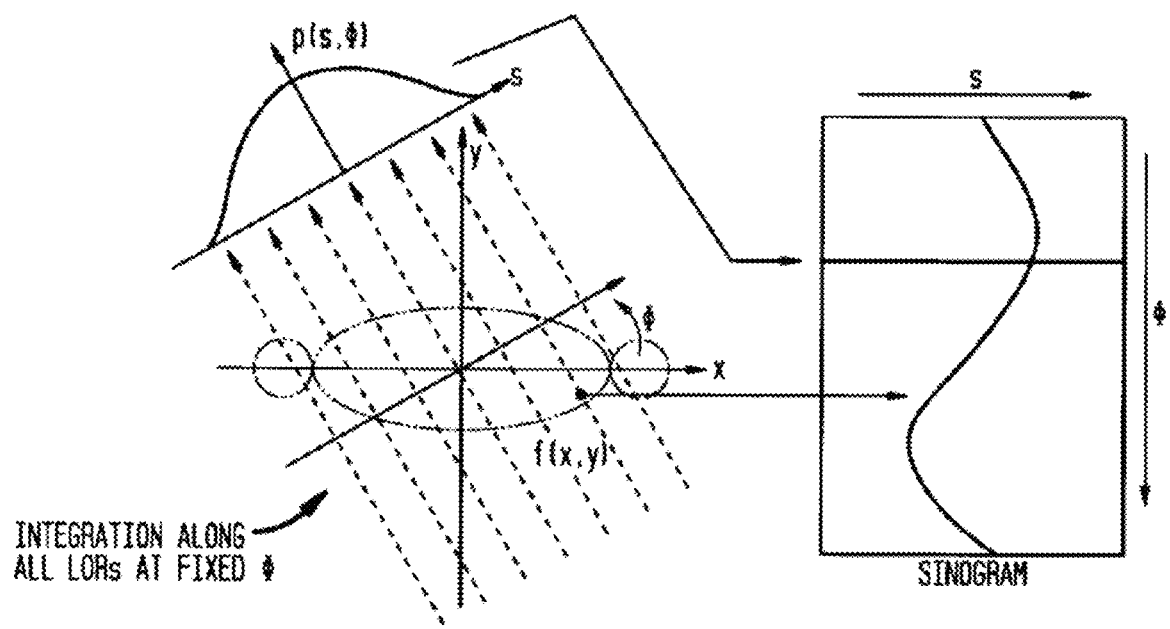
FIG. 1 is a diagram illustrating the relationship between PET projection data and a sinogram.
Figure 2:
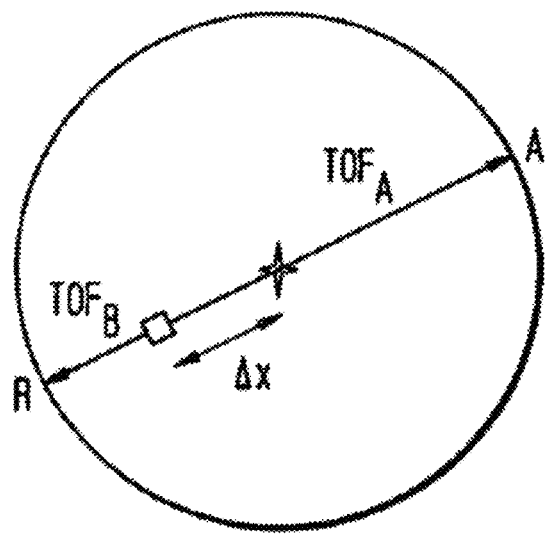
FIG. 2 is a diagram illustrating the concept of time of flight in PET imaging.
Figure 3:
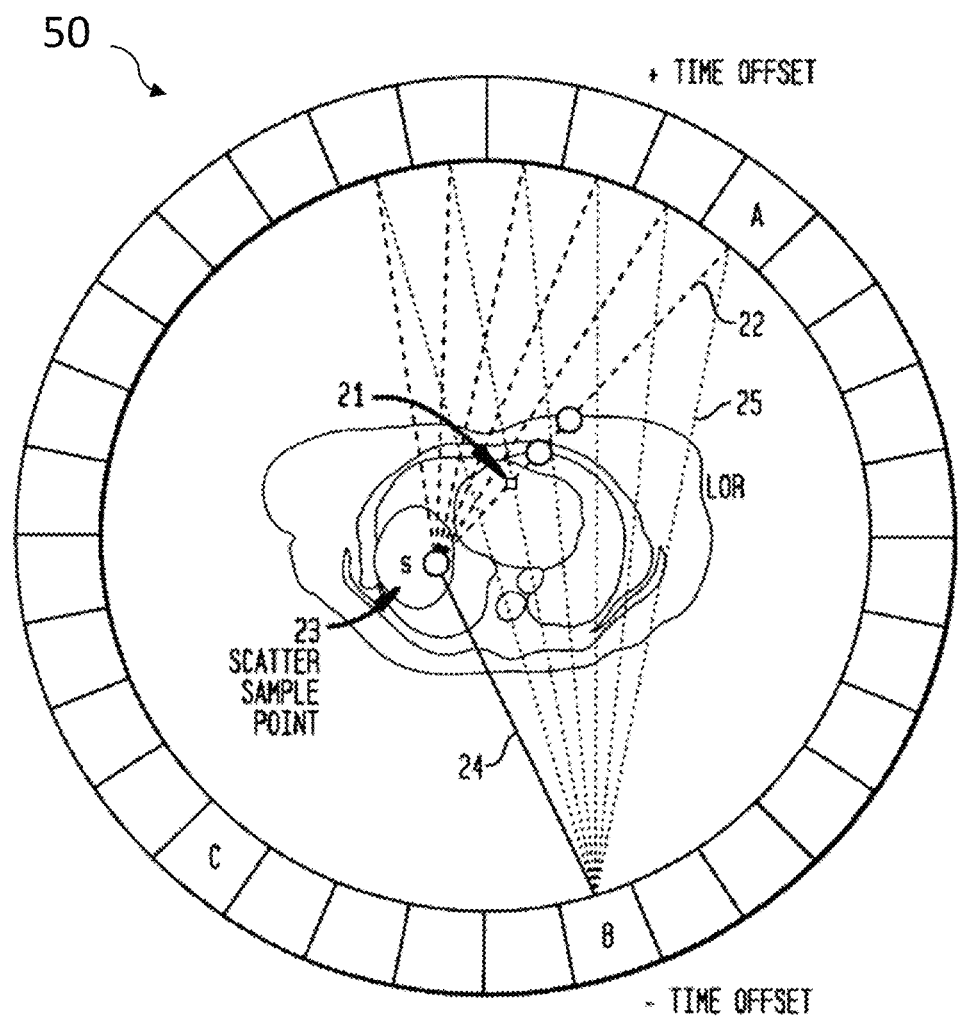
FIG. 3 is a diagram illustrating an example of a trajectory for a single scattering coincidence event.
Figure 19:
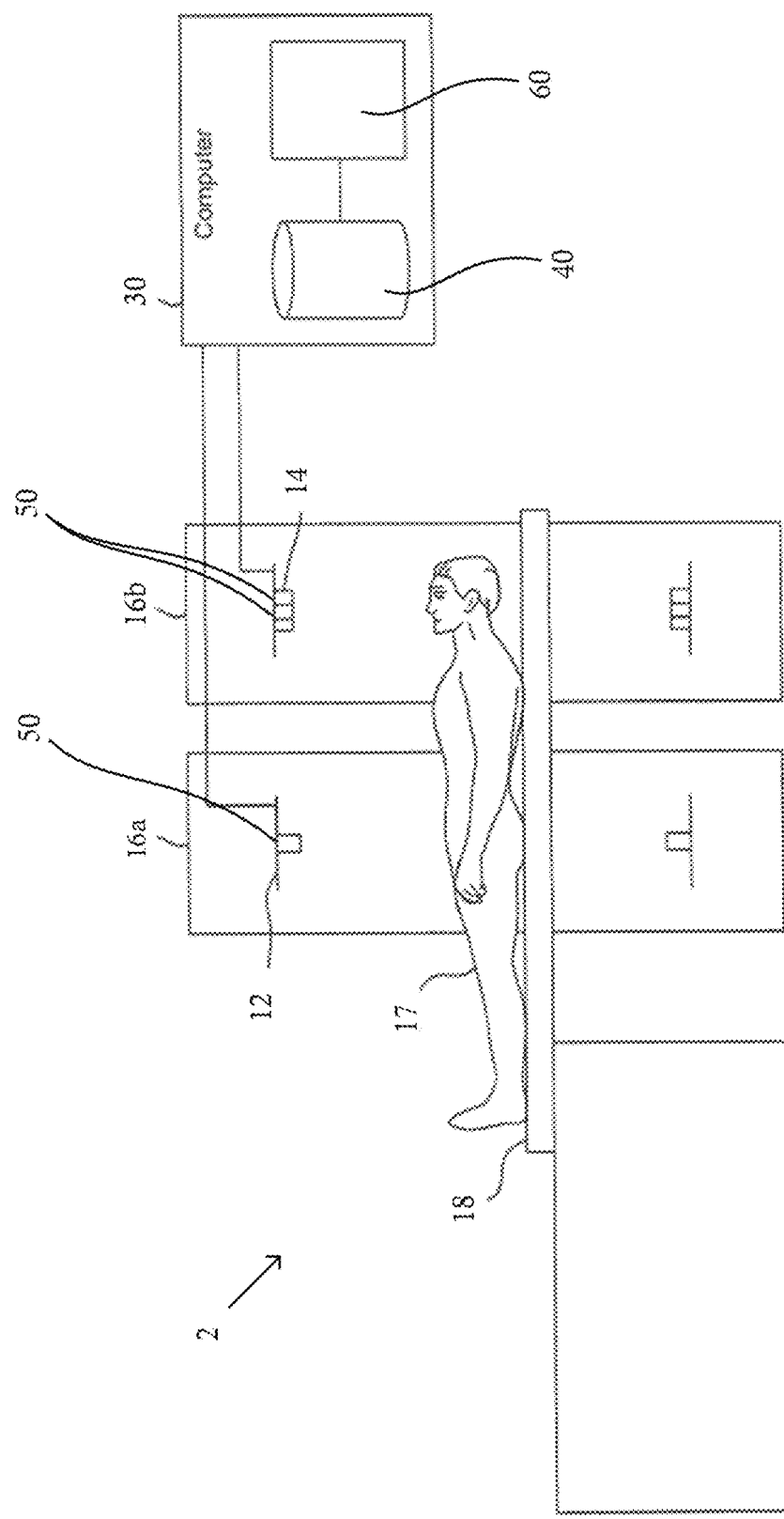
FIG. 19 is a high-level block diagram of a PET scanner system.

FIG. 19 illustrates one embodiment of a nuclear imaging system 2. The nuclear imaging system 2 includes a scanner for a PET modality 12 provided in a first gantry 16a. A patient 17 lies on a movable patient bed 18 that can be movable with respect to the first gantry 16a. The PET modality 12 includes a plurality of detectors 50 configured to detect an annihilation photons. FIGS. 3 and 4 show the detectors 50 in their ring configuration.

Scan data from the PET modality 12 is stored at one or more computer databases 40 and processed by one or more computer processors 60 of an accompanying computer system 30. The graphical depiction of the computer system 30 in FIG. 19 is provided by way of illustration only, and the computer system 30 may include one or more separate computing devices. The scan data can be provided by the PET modality 12, the second modality 14, and/or may be provided as a separate data set, such as, for example, from a memory coupled to the computer system 30. The computer system 30 can include one or more processing electronics for processing a signal received from the detectors 50.

The methods and system described herein can be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein.

Although the subject matter has been described in terms of exemplary embodiments, it is not limited thereto. Rather, the appended claims should be construed broadly, to include other variants and embodiments, which may be made by those skilled in the art.

What is claimed is:

1. A method for applying scatter correction to a scan data acquired in a time-of-flight positron emission tomography (TOF PET) scanner, the method comprising:

(A) selecting a pair of detector positions in the TOF PET scanner's detector ring;

(B) numerically estimating the double scatter coincidence event rate of annihilation photons in the selected pair of detector positions, wherein the annihilation photons in a double scatter coincidence event are assumed to be scattered once, each photon by a different scatter point in the TOF PET scanner's image volume, during a TOF PET acquisition scan period;

(C) selecting another pair of detector positions;

(D) repeating step (B) wherein the selected pair of detector positions is the another pair of detector positions;

(E) repeating steps (C) and (D) until all detector pairs of interest have been selected; and (F) scatter correcting the acquired scan data obtained from the pair of detector positions during the TOF PET acquisition scan period to reconstruct a TOF PET image based on the scan data.

2. The method of claim 1, wherein the selected pair of detector positions are $D_1$ and $D_2$, wherein the step (B) comprises:

a) selecting the two scatter points, $S_1$ and $S_2$, in the TOF PET scanner's image volume;

b) sampling values of the emission rate density between the two scatter points $S_1$ and $S_2$, determining the time of flight offset bin, n, for each contribution, and storing these values in a vector $R_n^{12}$;

c) calculating an exponential function of the negative of the line integral of the linear attenuation coefficients at energy $E_0$ between the two scatter points $S_1$ and $S_2$;

d) calculating the exponential function of the negative of the line integral of the linear attenuation coefficients at energy $E_1$ between $S_1$ and $D_1$;

e) calculating the exponential function of the negative of the line integral of the linear attenuation coefficients at energy $E_2$ between $S_2$ and $D_2$;

f) calculating the reciprocals of the squares of the distances from $S_1$ to $S_2$, from $S_1$ to $D_1$, and from $S_2$ to $D_2$;

g) calculating the linear attenuation coefficients at energy $E_0$, at the points $S_1$ and $S_2$;

h) calculating the ratio of the differential Compton cross section for a photon at energy $E_0$ to scatter to an energy $E_1$ to its total Compton cross section;

i) calculating the ratio of the differential Compton cross section for a photon at energy $E_0$ to scatter to an energy $E_2$ to its total Compton cross section;

j) calculating the geometrical cross section of detector $D_1$ for the photon traveling from $S_1$;

k) calculating the geometrical cross section of detector $D_2$ for the photon traveling from $S_2$;

l) calculating the detection efficiency of detector $D_1$ for the photon traveling from $S_1$ with energy $E_1$;

m) calculating the detection efficiency of detector $D_2$ for the photon traveling from $S_2$ with energy $E_2$;

n) calculating the image sample volumes associated with $S_1$ and with $S_2$;

o) multiplying the quantities computed in b) through n) together to get one contribution to the double scatter count rate for the detector pair $D_1$, $D_2$ for each sampled time of flight offset bin in;

p) selecting another pair of distinct scatter points $S_1$ and $S_2$, repeating steps a) through o) and adding the results to the previous results in $R_n^{12}$; and q) repeating step p) until the entire image volume has been adequately sampled by both $S_1$ and $S_2$.

3. The method of claim 2, wherein the computed line integrals, Compton cross sections, geometrical cross sections, detector efficiencies and scatter point positions are cached for reuse.

4. The method of claim 2, wherein each scatter point is chosen randomly within a cell of a regular spatial grid, one point per cell.

5. The method of claim 4, wherein a subset of all possible scatter point pairs is used for the calculation.

6. A method for applying scatter correction to a scan data acquired in a time-of-flight positron emission tomography (TOF PET) scanner, the method comprising:

(A) selecting a pair of detector positions in the TOF PET scanner's detector ring;

(B) numerically estimating the double scatter coincidence event rate of annihilation photons in the selected pair of detector positions, wherein one of the pair of annihilation photons in a double scatter coincidence event is assumed not to be scattered and the other of the two photons is scattered twice by a scatter point in the TOF PET scanner's image volume, during a TOF PET acquisition scan period;

(C) selecting another pair of detector positions;

(D) repeating step (B) wherein the pair of detector positions is the another pair of detector positions;

(E) repeating steps (C) and (D) until all detector pairs of interest have been selected; and (F) scatter correcting the acquired scan data obtained from the pair of detector positions during the TOF PET acquisition scan period to reconstruct a TOF PET image based on the scan data.

7. The method of claim 6, wherein the selected pair of detector positions are $D_1$ and $D_2$, wherein the step (B) comprises:

a) selecting the two scatter points $S_1$ and $S_2$ in the TOF PET scanner's image volume;

b) sampling values of the emission rate density between $D_1$ and $S_1$, determining the time of flight offset bin, n, for each sample, and storing these values in a vector quantity $R_n^{11}$;

c) calculating an exponential function of the negative of the line integral of the linear attenuation coefficients at energy $E_0$ between $D_1$ and $S_1$;

d) calculating the exponential function of the negative of the line integral of the linear attenuation coefficients at energy $E_1$ between $S_1$ and $S_2$;

e) calculating the exponential function of the negative of the line integral of the linear attenuation coefficients at energy $E_{12}$ between $S_2$ and $D_2$;

f) calculating the reciprocals of the squares of the distances from $S_1$ to $S_2$, from $S_1$ to $D_1$, and from $S_2$ to $D_2$;

g) calculating the linear attenuation coefficients for energy $E_0$ at $S_1$ and for $E_1$ at $S_2$;

h) calculating the ratio of the differential Compton cross section for a photon at energy $E_0$ to scatter to an energy $E_1$ to its total Compton cross section;

i) calculating the ratio of the differential Compton cross section for a photon at energy $E_1$ to scatter to an energy $E_{12}$ to its total Compton cross section;

j) calculating the geometrical cross section of detector $D_1$ for a photon pair produced between $D_1$ and $S_1$;

k) calculating the geometrical cross section of detector $D_2$ for the photon traveling from $S_2$;

l) calculating the detection efficiency of detector $D_1$ for the photon traveling from the emission point with energy $E_0$;

m) calculating the detection efficiency of detector $D_2$ for the photon traveling from $S_2$ with energy $E_{12}$;

n) calculating the image sample volumes associated with $S_1$ and with $S_2$;

o) multiplying the quantities computed in b) through n) together to get one contribution to the double scatter count rate for the detector pair $D_1$, $D_2$ for each sampled time of flight offset bin in $R_n^{11}$;

p) selecting another pair of distinct scatter points $S_1$ and $S_2$, repeating steps a) through o) and adding the results to the previous results in $R_n^{11}$; and q) repeating step p) until the entire image volume has been adequately sampled by both $S_1$ and $S_2$.

8. The method of claim 7, wherein the computed line integrals, Compton cross sections, geometrical cross sections, detector efficiencies, and scatter point positions are cached for reuse.

9. The method of claim 7, wherein each scatter point is chosen randomly within a cell of a regular spatial grid, one point per cell.

10. The method of claim 9, wherein a subset of all possible scatter point pairs is used for the calculation.

11. The method of claim 7, wherein the steps a) through Q) are performed with the following substitutions of the variables: $D_1 \leftrightarrow D_2$, $S_1 \leftrightarrow S_2$, $E_1 \rightarrow E_2$, and $R_n^{11} \rightarrow R_n^{22}$.

12. The method of claim 11, wherein the computed line integrals, Compton cross sections, geographical cross sections, detector efficiencies and scatter point positions are cached for reuse.

13. The method of claim 11, wherein each scatter point is chosen randomly within a cell of a regular spatial grid, one point per cell.

14. The method of claim 13, wherein a subset of all possible scatter point pairs is used for the calculation.

15. A system for processing and reconstructing time-of-flight positron emission tomography (TOF PET) sinogram data, comprising:
- a processor capable of executing instructions; and
- a non-transitory, machine readable storage medium encoded with program instructions for controlling a TOF PET scanner, such that when the processor executes the program instructions, the processor performs a method for applying scatter correction to a scan data acquired in the TOF PET scanner, the method comprising:
  - (A) selecting a pair of detector positions in the TOF PET scanner's detector ring;
  - (B) numerically estimating the double scatter coincidence event rate of annihilation photons in the selected pair of detector positions, wherein the annihilation photons in a double scatter coincidence event are assumed to be scattered once, each photon by a different scatter point in the TOF PET scanner's image volume, during a TOF PET acquisition scan period; and
  - (C) selecting another pair of detector positions;
  - (D) repeating step (B) wherein the selected pair of detector positions is the another pair of detector positions;
  - (E) repeating steps (C) and (D) until all detector pairs of interest have been selected; and
  - (F) scatter correcting the acquired scan data obtained from the pair of detector positions during the TOF PET acquisition scan period to reconstruct a TOF PET image based on the scan data.

16. A non-transitory, machine readable storage medium encoded with program instructions for controlling a time-of-flight positron emission tomography (TOF PET) scanner, such that when a processor executes the program instructions, the processor performs a method for applying scatter correction to a scan data acquired in the TOF PET scanner, the method comprising:
- (A) selecting a pair of detector positions in the TOF PET scanner's detector ring;
- (B) numerically estimating the double scatter coincidence event rate of annihilation photons in the selected pair of detector positions, wherein the annihilation photons in a double scatter coincidence event are assumed to be scattered once, each photon by a different scatter point in the TOF PET scanner's image volume, during a TOF PET acquisition scan period; and
- (C) selecting another pair of detector positions;
- (D) repeating step (B) wherein the selected pair of detector positions is the another pair of detector positions;
- (E) repeating steps (C) and (D) until all detector pairs of interest have been selected; and
- (F) scatter correcting the acquired scan data obtained from the pair of detector positions during the TOF PET acquisition scan period to reconstruct a TOF PET image based on the scan data.

17. A system for processing and reconstructing time-of-flight positron emission tomography (TOF PET) sinogram data, comprising:
- a processor capable of executing instructions; and
- a non-transitory, machine readable storage medium encoded with program instructions for controlling a TOF PET scanner, such that when the processor executes the program instructions, the processor performs a method for applying scatter correction to a scan data acquired in the TOF PET scanner, the method comprising:
  - (A) selecting a pair of detector positions in the TOF PET scanner's detector ring;
  - (B) numerically estimating the double scatter coincidence event rate of annihilation photons in the selected pair of detector positions, wherein one of the pair of annihilation photons in a double scatter coincidence event is assumed not to be scattered and the other of the two photons is scattered twice by a scatter point in the TOF PET scanner's image volume, during a TOF PET acquisition scan period;
  - (C) selecting another pair of detector positions;
  - (D) repeating step (B) wherein the pair of detector positions is the another pair of detector positions;
  - (E) repeating steps (C) and (D) until all detector pairs of interest have been selected; and
  - (F) scatter correcting the acquired scan data obtained from the pair of detector positions during the TOF PET acquisition scan period to reconstruct a TOF PET image based on the scan data.

18. A non-transitory, machine readable storage medium encoded with program instructions for controlling a time-of-flight positron emission tomography (TOF PET) scanner, such that when a processor executes the program instructions, the processor performs a method for applying scatter correction to a scan data acquired in the TOF PET scanner, the method comprising:
- (A) selecting a pair of detector positions in the TOF PET scanner's detector ring;
- (B) numerically estimating the double scatter coincidence event rate of annihilation photons in the selected pair of detector positions, wherein one of the pair of annihilation photons in a double scatter coincidence event is assumed not to be scattered and the other of the two photons is scattered twice by a scatter point in the TOF PET scanner's image volume, during a TOF PET acquisition scan period;
- (C) selecting another pair of detector positions;
- (D) repeating step (B) wherein the pair of detector positions is the another pair of detector positions;
- (E) repeating steps (C) and (D) until all detector pairs of interest have been selected; and
- (F) scatter correcting the acquired scan data obtained from the pair of detector positions during the TOF PET acquisition scan period to reconstruct a TOF PET image based on the scan data.

* * * * *